US008568968B2

(12) United States Patent
Lenz

(10) Patent No.: US 8,568,968 B2
(45) Date of Patent: Oct. 29, 2013

(54) EGFR POLYMORPHISMS PREDICT GENDER-RELATED TREATMENT

(75) Inventor: Heinz-Josef Lenz, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 281 days.

(21) Appl. No.: 12/758,763

(22) Filed: Apr. 12, 2010

(65) Prior Publication Data

US 2010/0286179 A1   Nov. 11, 2010

Related U.S. Application Data

(60) Provisional application No. 61/168,905, filed on Apr. 13, 2009.

(51) Int. Cl.
*C12Q 1/00* (2006.01)
(52) U.S. Cl.
USPC .............................. 435/4; 424/277.1; 436/64
(58) Field of Classification Search
None
See application file for complete search history.

(56) References Cited

U.S. PATENT DOCUMENTS

2006/0094012 A1   5/2006   Lenz et al.
2006/0094068 A1   5/2006   Bacus et al.
2006/0115827 A1   6/2006   Lenz

FOREIGN PATENT DOCUMENTS

| WO | WO 2004/011625 A2 | 2/2004 |
| WO | WO 2005/017493 A2 | 2/2005 |
| WO | WO 2005/120512 A2 | 12/2005 |
| WO | WO 2005/121380 A1 | 12/2005 |
| WO | WO 2008/088854 A2 | 7/2008 |
| WO | WO 2008/088860 A2 | 7/2008 |
| WO | WO 2008/088861 A2 | 7/2008 |
| WO | WO 2008/088876 A2 | 7/2008 |
| WO | WO 2008/088893 A2 | 7/2008 |
| WO | WO 2008/089465 A2 | 7/2008 |
| WO | WO 2009/140556 A2 | 11/2009 |
| WO | WO 2010/124264 A2 | 10/2010 |
| WO | WO 2010/124265 A1 | 10/2010 |

OTHER PUBLICATIONS

Press et al, Cancer Research 68:3037-42, Pub online Apr. 15, 2008.*
Wang et al, Clin Cancer Res 13:3597-3604, Pub online, Jun. 15, 2007.*
Zhang et al Translational Medicine Clinical Colorectal Cancer Jul. 2005 5: 124-131.*
Lenz, H-J. (2004) "The Use and Development of Germline Polymorphisms in Clinical Oncology," Journal of Clinical Oncology 22(13):2519-2521.
Konecny, G.E. et al. (2006) "Activity of the Dual Kinase Inhibitor Lapatinib (GW572016) against HER-2-Overexpressing and Trastuzumab-Treated Breast Cancer Cells," Cancer Res 66(3):1630-1639.
Burris, H.A., III (2004) "Dual Kinase Inhibition in the Treatment of Breast Cancer: Initial Experience with the EGFR/ErbB-2 Inhibitor Lapatinib," The Oncologist 9(3):10-15.
Burris, H.A., III (2005) "Phase I Safety, Pharmacokinetics, and Clinical Activity Study of Lapatinib (GW572016), a Reversible Dual Inhibitor of Epidermal Growth Factor Receptor Tyrosine Kinases, in Heavily Pretreated Patients with Metastatic Carcinomas," J. Clin. Oncol. 23(23):5305-5313.
Zhang, W. et al. (2005) "Gene Polymorphisms of Epidermal Growth Factor Receptor and its Downstream Effector, Interleukin-8, Predict Oxaliplatin Efficacy in Patients with Advanced Colorectal Cancer," Clinical Colorectal Cancer 5(2):124-131.
Zhang, W. et al. (2005) "Cyclin D1 and epidermal growth factor polymorphisms associated with survival in patients with advanced colorectal cancer treated with Cetuximab," Pharmacogenetics and Genomics 16:475-483.
Lievre, A. et al. (2006) "*KRAS* Mutation Status Is Predictive of Response to Cetuximab Therapy in Colorectal Cancer," Cancer Res. 66(8):3992-3995.
Baselga, J. (2005) "Does epidermal growth factor receptor status predict activity of cetuximab in colorectal cancer patients?" Nature Clinical Practice, Oncology 2(5):284-285.
Nagashima, F. et al. (2007) "EGFR, Cox-2, and EGF polymorphisms associated with progression-free survival of EGFR-expressing metastatic colorectal cancer patients treated with single-agent cetuximab (IMCL-0144)," Journal of Clinical Oncology, 2007 ASCO Annual Meeting Proceedings 25(18S):4129.
Lenz, H-J. et al. (2006) "EGFR-Targeted Therapies in Solid Tumors," Retrieved from the internet from: URL: http://www.CancerPublications.com.
Ahmed, F.E. (2005) "Molecular markers that predict response to colon cancer therapy," Expert Rev. Mol. Diagn. 5(3):353-375.
Pander, J. et al. (2007) "Pharmacogenetics of EGFR and VEGF inhibition," Drug Discovery Today 12(23/24):1054-1060.
Vallbohmer, D. et al. (2005) "Molecular Determinants of Cetuximab Efficacy," J. Clin. Oncol. 23(15):3536-3544.
Hinoda, Y. et al. (2004) "Monoclonal antibodies as effective therapeutic agents for solid tumors," Cancer Sci 95(8):621-625.
Cunningham, D. et al. (2004) "Cetuximab Monotherapy and Cetuximab plus Irinotecan in Irinotecan-Refractory Metastatic Colorectal Cancer," N. Engl. J. Med. 351(4):337-345.
Wiedmann, M.W. et al. (2005) "Molecularly Targeted Therapy for Gastrointestinal Cancer," Current Cancer Drug Targets 5:171-193.
Matsubara, J. et al. (2008) "Impacts of excision repair cross-complementing gene I (ERCCI), dihydropyrimidine dehydrogenase, and epidermal growth factor receptor on the outcomes of patients with advanced gastric cancer," British Journal of Cancer 98:832-839.
Graziano, F. et al. (2008) "Pharmacogenetic Profiling for Cetuximab Plus Irinotecan Therapy in Patients With Refractory Advanced Colorectal Cancer," J. Clin. Oncol. 26:1427-1434.

(Continued)

*Primary Examiner* — Lei Yao
(74) *Attorney, Agent, or Firm* — Foley & Lardner LLP; Antoinette F. Konski; Alex Y. Nie

(57) ABSTRACT

The invention provides compositions and methods for identifying a gender-specific cancer patient suitable for treatment with various treatment regimens available to cancer patients. After determining if a patient is suitable for therapy, the invention also provides methods for treating these patients.

12 Claims, 4 Drawing Sheets

(56) References Cited

OTHER PUBLICATIONS

Shaye, O.S. et al. (2007) "Polymorphisms in angiogenesis related genes predict clinical outcome in patients (pts) with metastatic colorectal cancer (mCRC) treated with first line 5-FU or capecitabine in combination with oxaliplatin and bevacizumab (FOLFOX/BV or XELOX/BV)," Journal of Clinical Oncology, 2007 ASCO Annual Meeting Proceedings 25(18S):10576.
Manegold, P.C. et al. (2008) "ICAM-1, GRP-78, and NFkB gene polymorphisms and clinical outcome in patients (pts) with metastatic colorectal cancer (mCRC) treated with first line 5-FU or capecitabine in combination with oxaliplatin and bevacizumab (FOLFOX/BV or XELOX/BV)," Journal of Clinical Oncology, 2008 ASCO Annual Meeting Proceedings 26(15S):4134.
Adlard, J.W. et al. (2002) "Prediction of the response of colorectal cancer to systemic therapy," Lancet Oncol. 3:75-82.
Ning, Y. et al. (2009) "VEGF and VEGFR1 gene expression levels and tumor recurrence in adjuvant colon cancer," ASCO Annual Meeting 2009, Abstract No. 4040.
Yang, D. et al. (2006) "Gene Expression Levels of Epidermal Growth Factor Receptor, Survivin, and Vascular Endothelial Growth Factor as Molecular Markers of Lymph Node Involvement in Patients with Locally Advanced Rectal Cancer," Clinical Colorectal Cancer 6(4):305-311.
Schneider, S. et al. (2006) "Gene expression in tumor-adjacent normal tissue is associated with recurrence in patients with rectal cancer treated with adjuvant chemoradiation," Pharmacogenetics and Genomics 16:555-563.
Vallbohmer, D. et al. (2006) "Molecular determinants of irinotecan efficacy," Int. J. Cancer 119:2435-2442.
Lurje, G. et al. (2008) "Polymorphisms in VEGF and IL-8 predict tumor recurrence in stage III colon cancer," Annals of Oncology 19:1734-1741.
Scheithauer, W. et al. (2007) "Cetuximab plus irinotecan in patients (pts) with metastatic colorectal cancer (mCRC) failing prior oxaliplatin-based therapy: the EPIC trial," European Journal of Cancer, Supplement 5(4):235-236.
Kim, G.P. (2008) "Predictive Markers in Colorectal Cancer," Semin Colon Rectal Surg 19:231-238.
Zhang, W. et al. (2009) "Genetic variants in angiogenesis pathway associated with clinical outcome in NSCLC patients (pts) treated with bevacizumab in combination with carboplatin and paclitaxel: Subset pharmacogenetic analysis of ECOG 4599," ASCO Annual Meeting 2009, Abstract No. 8032.
Dean-Colomb, W. et al. (2008) "Her2-positive breast cancer: Herceptin and beyond," European Journal of Cancer 44:2806-2812.
Jain, M. et al. (2007) "Influence of Apoptosis (BCL2, FAS), Cell Cycle (CCND1) and Growth Factor (EGF, EGFR) Genetic Polymorphisms on Survival Outcome," Cancer Biology & Therapy 6(10):1553-1558.
Lurje, G. et al. (2010) "Genetic variations in angiogenesis pathway genes associated with clinical outcome in localized gastric adenocarcinoma," Annals of Oncology 21(1):78-86.
Yan, L. et al. (2005) "Pharmacogenetics and pharmacogenomics in oncology therapeutic antibody development," BioTechniques 39:565-568.
Allen, W.L. et al. (2006) "Predicting the outcome of chemotherapy for colorectal cancer," Current Opinion in Pharmacology 6:332-336.
Ng, K. et al. (2008) "Targeting the epidermal growth factor receptor in metastatic colorectal cancer," Critical Reviews in Oncology/Hematology 65:8-20.
Pasqualetti, G. et al. (2007) "Vascular endothelial growth factor pharmacogenetics: a new perspective for anti-angiogenic therapy," Pharmacogenomics 8(1):49-66.
Zhang, W. et al. (2002) "A polymorphic dinucleotide repeat in intron 1 of EGFR (epithelial growth factor receptor) gene is associated with clinical response to platinum based chemotherapy in patients with advanced colorectal disease," ASCO Annual Meeting 2002, Abstract No. 533.
Park, D.J. et al. (2003) "Tailoring chemotherapy in advanced colorectal cancer," Current Opinion in Pharmacology 3:378-385.
Gebhardt, F. et al. (1999) "Modulation of Epidermal Growth Factor Receptor Gene Transcription by a Polymorphic Dinucleotide Repeat in Intron 1," The Journal of Biological Chemistry 274(19):13176-13180.
Lurje, G. et al. (2008) "Polymorphisms in *Cyclooxygenase-2* and *Epidermal Growth Factor Receptor* Are Associated with Progression-Free Survival Independent of K-ras in Metastatic Colorectal Cancer Patients Treated with Single-Agent Cetuximab," Clin. Cancer Res. 14(23):7884-7895.
Gold, P.J. et al. (2010) "Cetuximab as second-line therapy in patients with metastatic esophageal adenocarcinoma: A phase II Southwest Oncology Group Study (S0415)," J Thorac Oncol. 5(9):1472-1476.
Gerger, A. et al. (2011) "Pharmacogenetic angiogenesis profiling for first-line bevacizumab plus oxaliplatin-based chemotherapy in patients with metastatic colorectal cancer," Clin Cancer Res.:1-33.
Bonaccorsi et al. (2004), The androgen receptor associates with the epidermal growth factor receptor in androgen-sensitive prostate cancer cells, Steroids 69:549-552.
Buerger et al. (2000), Length and loss of heterozygosity of an intron 1 polymorphic sequence of EGFR is related to cytogenetic alterations and epithelial growth factor receptor expression, Cancer Res 60:854-857.
Decosse et al. (1993), Gender and colorectal cancer, Eur J Cancer Prev 2:105-115.
Elsaleh et al. (2000), Association of tumour site and sex with survival benefit from adjuvant chemotherapy in colorectal cancer, Lancet 355:1745-1750.
Fiorelli et al. (1999), Functional estrogen receptor β colon cancer cells, Biochem Biophys Res Commun 261:521-527.
Gebhardt et al. (1999), Modulation of epidermal growth factor receptor gene transcription by a polymorphic dinucleotide repeat in intron 1, J. Biol. Chem. 274(19):13176-13180.
Grodstein et al. (1999), Postmenopausal hormone therapy and the risk of colorectal cancer: a review and meta-analysis, Am J Med 106:574-582.
Hemming et al. (1992), Prognostic markers of colorectal cancer: an evaluation of DNA content, epidermal growth factor receptor, and Ki-67, J Surg Oncol 51:147-152.
Levi et al. (2005), Gender as a predictor for optimal dynamic scheduling of oxaliplatin, 5-fluorouracil and leucovorin in patients with metastatic colorectal cancer. Results from EORTC randomized phase III trial 05963, J Clin Oncol (Meeting Abstracts) 23:[abstract #3587].
Levin (2003), Bidirectional signaling between the estrogen receptor and the epidermal growth factor receptor, Mol Endocrinol 17:309-317.
Liu et al. (2003), Interethnic difference in the allelic distribution of human epidermal growth factor receptor intron 1 polymorphism, Clin Cancer Res 9:1009-1012.
Martin et al. (2002), Candidate genes colocalized to linkage regions in inflammatory bowel disease, Digestion 66:121-126.
Moriai et al. (1993), Cloning of a variant epidermal growth factor receptor. Biochem. Biophys. Res. Commun, 191(3):1034-1039.
Moriai et al. (1994), A variant epidermal growth factor receptor exhibits altered type α transforming growth factor binding and transmembrane signaling, Proc Natl Acad Sci U S A 91:10217-10221.
Ries et al. (2000), The annual report to the nation on the status of cancer, 1973-1997, with a special section on colorectal cancer, Cancer 88(10):2398-2424.
Rossouw et al. (2002), Risks and benefits of estrogen plus progestin in healthy postmenopausal women: principal results from the Women's Health Initiative randomized controlled trial, JAMA 288(3):321-333.
Wingo et al. (1998), Cancer incidence and mortality, 1973-1995: a report card for the U.S., Cancer 82(6):1197-1207.
Zhang et al. (2005), Epidermal growth factor receptor gene polymorphisms predict pelvic recurrence in patients with rectal cancer treated with chemoradiation, Clin Cancer Res 11:600-605.

\* cited by examiner

EGFR POLYMORPHISMS PREDICT GENDER-RELATED TREATMENT

CROSS-REFERENCE TO RELATED APPLICATIONS

This application claims the benefit under 35 U.S.C. §119 (e) of U.S. Provisional Application Ser. No. 61/168,905, filed Apr. 13, 2009, the contents of which is incorporated by reference into the present disclosure in its entirety.

STATEMENT OF GOVERNMENT SUPPORT

This invention was made with government support under Grant No. 5 K24CA827540 awarded by the National Institutes of Health. The government has certain rights in the invention.

FIELD OF THE INVENTION

This invention relates to the filed of pharmacogenomics and specifically to the application of genetic polymorphisms to diagnose and treat diseases.

BACKGROUND OF THE INVENTION

Colorectal cancer is the second most common cause of cancer-related death in the United States. In 2007, an estimated 153,760 new cases will be diagnosed and 52,180 deaths will occur (1). Epidermal growth factor receptor (EGFR), also known as HER-1 or erbB-1, is a transmembrane protein, a member of a human epithelial receptor tyrosine kinase family, and is widely expressed in colonic tissues (2). Activation of EGFR initiates signal transduction cascades that affect gene expression, cellular proliferation, inhibition of apoptosis, and angiogenesis (3). EGFR has shown prognostic value and is associated with poor survival, more aggressive behavior, and an increased risk of invasion/metastasis in colorectal cancers (4). Additionally, blocking EGFR ligand binding through interaction with therapeutic monoclonal antibody such as cetuximab and panitumumab has been shown to be an effective treatment for advanced colon cancer (5).

Two functional polymorphic variants of EGFR are known in the art. The first polymorphism is a single nucleotide change (G to A) leading to an arginine (Arg) to lysine (Lys) substitution in codon 497 (HER-1 R497K) in the extracellular domain within subdomain IV of the EGFR gene. An in vitro study has shown that the variant HER-1 497K has attenuated functions in ligand binding, growth stimulation, tyrosine kinase activation, and induction of proto-oncogenes (myc, fos, and jun) compared with the more prevalent "wild-type" HER-1 497R variant (6).

Another functional polymorphism is located within intron 1 of the EGFR gene. This polymorphism is associated with altering levels of EGFR transcription both in vitro and in vitro (7, 8). The length of this $(CA)_n$ dinucleotide polymorphism inversely correlates with transcriptional activity of the gene. In vitro models have shown more transcriptional activity in cell lines expressing the shorter polymorphic variant (16 CA repeats (SEQ ID NO: 1)) compared with the longer polymorphic variant (>20 CA repeats (SEQ ID NO: 2) (8)). In vitro human breast tumors seem to select the shorter number of CA repeats ensuring higher expression levels of EGFR, which in turn propagates tumor growth and development (7).

Considerable evidence is accumulating that supports gender-related differences in the development of colonic carcinomas, with women of all ages less likely to develop colon cancer (9-11). Large comprehensive studies such as the Women's Health Initiative have conclusively shown that postmenopausal women treated with estrogen replacement therapy have a significant reduction in both risk and rate of developing colon cancer (12, 13). The molecular mechanisms behind this protective effect against colon cancer are not fully understood. However, the colon does express both estrogen receptor β (14) and androgen receptor (15). Important functional linkage and bidirectional signaling between epidermal growth factor receptor (EGFR) and estrogen receptor have been shown (16). Important signaling regulation between EGFR and androgen receptor has also been shown (17). Because EGFR is affected by both female estrogen receptors (16) and male androgen receptors (17), EGFR may be a potential mediator of gender-related differences in colon cancer.

Although considerable research correlating polymorphisms has been reported, much work remains to be done. This invention supplements the existing body of knowledge and provides related advantages as well.

DESCRIPTION OF THE EMBODIMENTS

This invention provides methods to: 1) identify a gender-specific cancer patient suitable for a pyrimidine antimetabolite based therapy or 2) treat a gender-specific cancer patient by administration of a pyrimidine antimetabolite based therapy, by determining a genotype of a cell or tissue sample isolated from the patient for at least one polymorphism identified herein. The methods require detecting the identity of at least one polymorphism of a predetermined gene selected from the group identified in Table 1 below.

TABLE 1

Predictive Polymorphisms and Genotypes For Males and Females

| Gender | Allele (Polymorphism) | Predictive Genotype | Measured Response |
|---|---|---|---|
| Female | HER-1 (R497K) | Arg/Arg | Longer Overall Survival |
| Female | EGFR intron 1 $(CA)_n$ repeat | two alleles with a $(CA)_n$ repeat <20 (SEQ ID NO: 3) | Longer Overall Survival |
| Female | HER-1 (R497K) | Arg/Arg | Longer Overall Survival |
| | EGFR intron 1 $(CA)_n$ repeat | two alleles with a $(CA)_n$ repeat <20 (SEQ ID NO: 3) | |
| Female | HER-1 (R497K) | Arg/Arg | Longer Overall Survival |
| | EGFR intron 1 $(CA)_n$ repeat | at least 1 allele with a $(CA)_n$ repeat ≥20 (SEQ ID NO: 4) | |
| Female | HER-1 (R497K) | Arg/Lys or Lys/Lys | Longer Overall Survival |
| | EGFR intron 1 $(CA)_n$ repeat | two alleles with a $(CA)_n$ repeat <20 (SEQ ID NO: 3) | |

TABLE 1-continued

Predictive Polymorphisms and Genotypes For Males and Females

| Gender | Allele (Polymorphism) | Predictive Genotype | Measured Response |
|---|---|---|---|
| Male | HER-1 (R497K) | Arg/Lys or Lys/Lys | Longer Overall Survival |
| Male | EGFR intron 1 (CA)$_n$ repeat | at least 1 allele with a (CA)$_n$ repeat ≥20 (SEQ ID NO: 4) | Longer Overall Survival |
| Male | HER-1 (R497K) EGFR intron 1 (CA)$_n$ repeat | Arg/Lys or Lys/Lys at least 1 allele with a (CA)$_n$ repeat ≥20 (SEQ ID NO: 4) | Longer Overall Survival |
| Male | HER-1 (R497K) EGFR intron 1 (CA)$_n$ repeat | Arg/Arg at least 1 allele with a (CA)$_n$ repeat ≥20 (SEQ ID NO: 4) | Longer Overall Survival |
| Male | HER-1 (R497K) EGFR intron 1 (CA)$_n$ repeat | Arg/Lys or Lys/Lys two alleles with a (CA)$_n$ repeat <20 (SEQ ID NO: 3) | Longer Overall Survival |

The various embodiments are set forth herein.

In one embodiment, the inventions provides a method for identifying a female cancer patient suitable for a pyrimidine antimetabolite based therapy, comprising determining a genotype of a cell or tissue sample isolated from the patient for at least one polymorphism of HER-1 (R497K) or EGFR intron 1 (CA)$_n$ repeat, wherein the genotype of one or more of Arg/Arg for HER-1 (R497K); or two alleles with a (CA)$_n$ repeat <20 (SEQ ID NO: 3) for EGFR intron 1 (CA)$_n$ repeat, identifies the patient as suitable for the therapy, or the genotype of one or more of Arg/Lys or Lys/Lys for HER-1 (R497K); or at least 1 allele with a (CA)$_n$ repeat ≥20 (SEQ ID NO: 4) for EGFR intron 1 (CA)$_n$ repeat, identifies the patient as not suitable for the therapy.

In another embodiment, the invention provides a method for identifying a female cancer patient suitable for a pyrimidine antimetabolite based therapy, comprising determining a genotype of a cell or tissue sample isolated from the patient for both HER-1 (R497K) and EGFR intron 1 (CA)$_n$ repeat polymorphisms, wherein the genotype of: Arg/Arg for HER-1 (R497K) and two alleles with a (CA)$_n$ repeat <20 (SEQ ID NO: 3) for EGFR intron 1 (CA)$_n$ repeat; Arg/Arg for HER-1 (R497K) and at least 1 allele with a (CA)$_n$ repeat ≥20 (SEQ ID NO: 4) for EGFR intron 1 (CA)$_n$ repeat; or Arg/Lys or Lys/Lys for HER-1 (R497K) and two alleles with a (CA)$_n$ repeat <20 (SEQ ID NO: 3) for EGFR intron 1 (CA)$_n$ repeat, identifies the patient as suitable for the therapy, or the genotype of: Arg/Lys or Lys/Lys for HER-1 (R497K) and at least 1 allele with a (CA)$_n$ repeat ≥20 (SEQ ID NO: 4) for EGFR intron 1 (CA)$_n$ repeat, identifies the patient as not suitable for the therapy.

In another embodiment, the invention provides a method for identifying a male cancer patient suitable for a pyrimidine antimetabolite based therapy, comprising determining a genotype of a cell or tissue sample isolated from the patient for at least one polymorphism of HER-1 (R497K) or EGFR intron 1 (CA)$_n$ repeat, wherein the genotype of one or more of: Arg/Lys or Lys/Lys for HER-1 (R497K); or at least 1 allele with a (CA)$_n$ repeat ≥20 (SEQ ID NO: 4) for EGFR intron 1 (CA)$_n$ repeat, identifies the patient as suitable for the therapy, or the genotype of one or more of: Arg/Arg for HER-1 (R497K); or two alleles with a (CA)$_n$ repeat <20 (SEQ ID NO: 3) for EGFR intron 1 (CA)$_n$ repeat, identifies the patient as not suitable for the therapy.

In another embodiment, the invention provides a method for identifying a male cancer patient suitable for a pyrimidine antimetabolite based therapy, comprising determining a genotype of a cell or tissue sample isolated from the patient for both HER-1 (R497K) and EGFR intron 1 (CA)$_n$ repeat polymorphisms, wherein the genotype of: Arg/Lys or Lys/Lys for HER-1 (R497K) and at least 1 allele with a (CA)$_n$ repeat ≥20 (SEQ ID NO: 4) for EGFR intron 1 (CA)$_n$ repeat; Arg/Arg for HER-1 (R497K) and at least 1 allele with a (CA)$_n$ repeat ≥20 (SEQ ID NO: 4) for EGFR intron 1 (CA)$_n$ repeat; or Arg/Lys or Lys/Lys for HER-1 (R497K) and two alleles with a (CA)$_n$ repeat <20 (SEQ ID NO: 3) for EGFR intron 1 (CA)$_n$ repeat, identifies the patient as suitable for the therapy, or the genotype of: Arg/Arg for HER-1 (R497K) and two alleles with a (CA)$_n$ repeat <20 (SEQ ID NO: 3) for EGFR intron 1 (CA)$_n$ repeat, identifies the patient as not suitable for the therapy.

In one aspect of the above embodiments, the cancer patient is suffering from a cancer of the type of the group: lung cancer, breast cancer, head and neck cancer, ovarian cancer, rectal cancer, colorectal cancer, colon cancer, metastatic colon cancer, advanced colon cancer, non-small cell lung cancer (NSCLC), advanced gastric cancer, metastatic gastric cancer, advanced hepatocarcinoma, metastatic liver cancer, metastatic intra-abdominal cancer, bone cancer, stomach cancer, spleen cancer, pancreatic cancer, gallbladder cancer or solid tumors.

In another aspect of the above embodiments, the pyrimidine antimetabolite based therapy comprises administration of 5-fluorouracil (5-FU) or an equivalent thereof. In a further aspect, the therapy comprises administration of 5-FU and irinotecan (CPT-11) or an equivalent thereof. In yet another further aspect, the therapy further comprises administration of oxaliplatin or an equivalent thereof.

In yet another aspect of the above embodiments, the patient identified as suitable for the therapy is likely to experience relatively longer overall survival. In a further aspect, a patient having a genotype of a group that is likely to experience a relatively longer overall survival is a patient that is likely to experience a relatively longer overall survival than patients suffering from a same cancer and receiving the therapy and not having a genotype of the group.

In another embodiment, the invention provides a method for treating a female cancer patient, comprising: determining the genotype of a cell or tissue sample isolated from the patient for at least one polymorphism of HER-1 (R497K) or EGFR intron 1 (CA)$_n$ repeat; and administering to a patient, identified as having the genotype of Arg/Arg for HER-1 (R497K) or two alleles with a (CA)$_n$ repeat <20 (SEQ ID NO: 3) for EGFR intron 1 (CA)$_n$ repeat, a pyrimidine antimetabolite based treatment, thereby treating the patient.

In another embodiment, the invention provides a method for treating a female cancer patient, comprising: determining the genotype of a cell or tissue sample isolated from the patient for a genotype of both HER-1 (R497K) and EGFR intron 1 (CA)$_n$ repeat polymorphisms; and administering to a patient, identified as having the genotype of Arg/Arg for HER-1 (R497K) and two alleles with a $(CA)_n$ repeat <20 (SEQ ID NO: 3) for EGFR intron 1 $(CA)_n$ repeat; Arg/Arg for HER-1 (R497K) and at least 1 allele with a $(CA)_n$ repeat ≥20 (SEQ ID NO: 4) for EGFR intron 1 $(CA)_n$ repeat; or Arg/Lys or Lys/Lys for HER-1 (R497K) and two alleles with a $(CA)_n$ repeat <20 (SEQ ID NO: 3) for EGFR intron 1 $(CA)_n$ repeat, a pyrimidine antimetabolite based therapy, thereby treating the patient.

In another embodiment, the invention provides a method for treating a male cancer patient, comprising: determining a genotype of a cell or tissue sample isolated from the patient for at least one polymorphism of HER-1 (R497K) or EGFR intron 1 $(CA)_n$ repeat; and administering to a patient having the genotype of Arg/Lys or Lys/Lys for HER-1 (R497K) or at least 1 allele with a $(CA)_n$ repeat ≥20 (SEQ ID NO: 4) for EGFR intron 1 $(CA)_n$ repeat a pyrimidine antimetabolite based treatment, thereby treating the patient.

In another embodiment, the invention provides a method for treating a male cancer patient, comprising: determining a genotype of a cell or tissue sample isolated from the patient for a genotype of both HER-1 (R497K) and EGFR intron 1 $(CA)_n$ repeat polymorphisms; and administering to a patient, having the genotype of Arg/Lys or Lys/Lys for HER-1 (R497K) and at least 1 allele with a $(CA)_n$ repeat ≥20 (SEQ ID NO: 4) for EGFR intron 1 $(CA)_n$ repeat; Arg/Arg for HER-1 (R497K) and at least 1 allele with a $(CA)_n$ repeat ≥20 (SEQ ID NO: 4) for EGFR intron 1 $(CA)_n$ repeat; or Arg/Lys or Lys/Lys for HER-1 (R497K) and two alleles with a $(CA)_n$ repeat <20 (SEQ ID NO: 3) for EGFR intron 1 $(CA)_n$ repeat, a pyrimidine antimetabolite based treatment, thereby treating the patient.

In one aspect of the above embodiments, the cancer patient is suffering from a cancer of the type of the group: lung cancer, breast cancer, head and neck cancer, ovarian cancer, rectal cancer, colorectal cancer, colon cancer, metastatic colon cancer, advanced colon, cancer non-small cell lung cancer (NSCLC), advanced gastric cancer, metastatic gastric cancer, advanced hepatocarcinoma, metastatic liver cancer, metastatic intra-abdominal cancer, bone cancer, stomach cancer, spleen cancer, pancreatic cancer, gallbladder cancer or solid tumors.

In another aspect of the above embodiments, the pyrimidine antimetabolite based therapy comprises administration of 5-fluorouracil (5-FU) or an equivalent thereof. In a further aspect, the therapy comprises administration of 5-FU and irinotecan (CPT-11) or an equivalent thereof. In yet another further aspect, the therapy further comprises administration of oxaliplatin or an equivalent thereof.

In yet another aspect of the above embodiments, the patient identified as suitable for the therapy is likely to experience relatively longer overall survival. In a further aspect, a patient having a genotype of a group that is likely to experience a relatively longer overall survival is a patient that is likely to experience a relatively longer overall survival than patients suffering from a same cancer and receiving the therapy and not having a genotype of the group.

To practice the above methods, the sample is a patient sample containing a tumor cell, a normal cell adjacent to a tumor, a normal cell corresponding to a tumor tissue type, a blood cell, peripheral blood lymphocyte or combinations thereof. These methods are not limited by the technique that is used to identify the polymorphism of interest. Suitable methods include but are not limited to the use of hybridization probes, antibodies, primers for PCR analysis and gene chips and software for high throughput analysis. Additional polymorphisms can be assayed and used as negative controls.

In one aspect, the method requires isolating a sample containing the genetic material to be tested; however, it is conceivable that one of skill in the art will be able to analyze and identify genetic polymorphisms in situ at some point in the future. Accordingly, the inventions of this application are not to be limited to requiring isolation of the genetic material prior to analysis.

This invention also provides a panel, kit, software and/or gene chip for patient sampling and performance of the methods of this invention. The kits contain panels, gene chips, probes and/or primers that can be used to amplify and/or for determining the molecular structure of the polymorphisms identified above. In an alternate embodiment, the kit contains antibodies and/or other polypeptide binding agents that are useful to identify a polymorphism of Table 1. Instructions for using the materials to carry out the methods are further provided.

The present invention provides methods and kits for identifying a cancer patient suitable for a pyrimidine antimetabolite based therapy. The methods require determining the subject's genotype at the gene of interest. The present invention also provides use of a pyrimidine antimetabolite based therapy for the treatment of a patient selected for longer overall survival to the therapy based on the methods described herein. Other aspects of the invention are described below or will be apparent to one of skill in the art in light of the present disclosure.

This invention also provides for a prognostic panel of genetic markers selected from, but not limited to the genetic polymorphisms identified in Table 1. The prognostic panel comprises probes or primers that can be used to amplify and/or for determining the molecular structure of the polymorphisms identified above. The probes or primers can be attached or supported by a solid phase support such as, but not limited to a gene chip or microarray. The probes or primers can be detectably labeled. This aspect of the invention is a means to identify the genotype of a patient sample for the genes of interest identified above.

BRIEF DESCRIPTION OF THE FIGURES

Four figures are attached to this application. The figures graphically illustrate the results of the experimental example.

MODES FOR CARRYING OUT THE INVENTION

Figure 1:
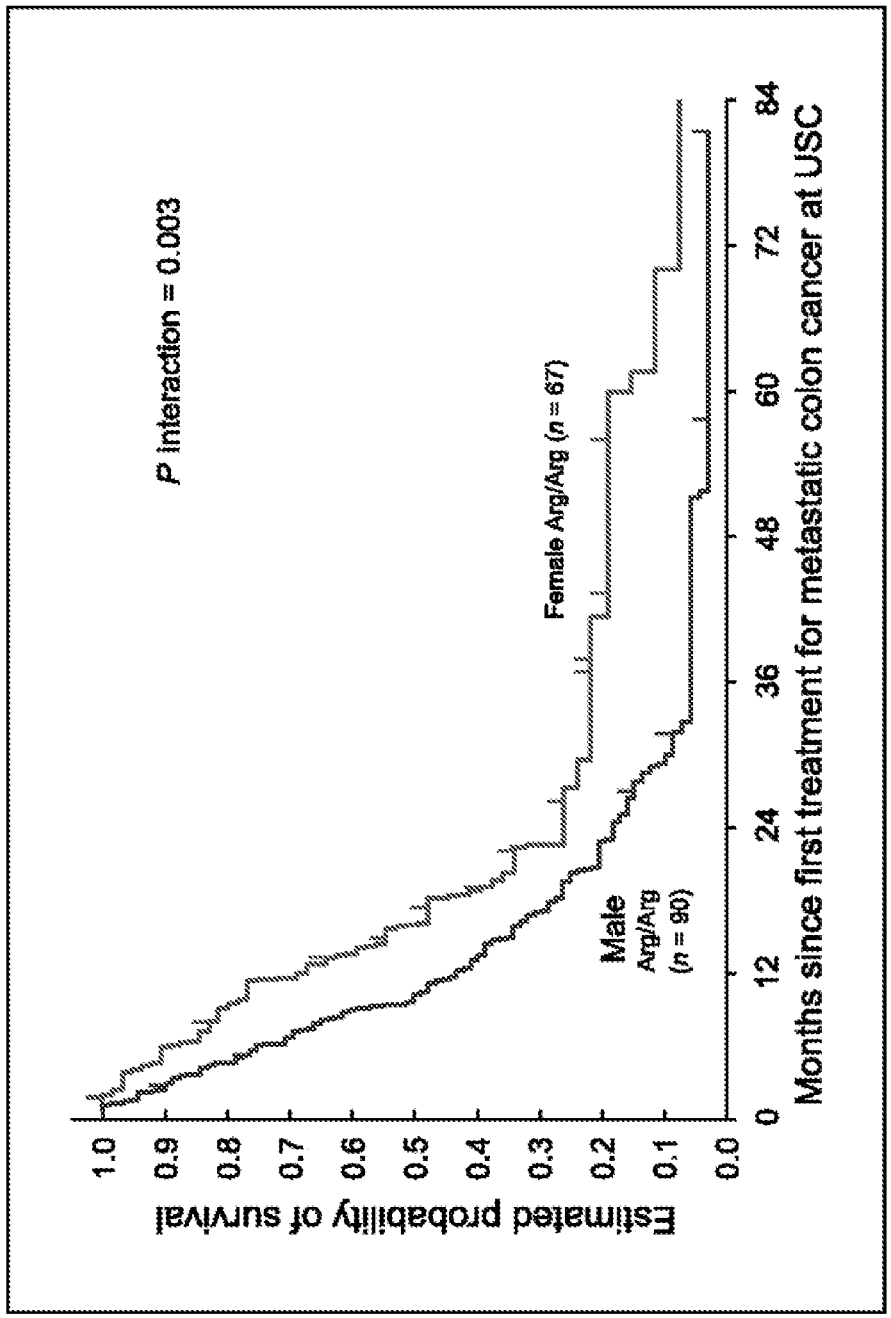
FIG. 1 shows gender-related overall survival associated with the HER-1 Arg/Arg genotype. The top curve indicates female patients having the Arg/Arg genotype, while the bottom curve indicates male patients having the Arg/Arg genotype. The designation n represents the number of patients. The X-axis indicates the number of months since a patient first received treatment for metastatic colon cancer at the University of Southern California (USC). The Y-axis indicates the estimated probability of survival. The P interaction value is equal to 0.003.

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

The practice of the present invention employs, unless otherwise indicated, conventional techniques of molecular biology (including recombinant techniques), microbiology, cell biology, biochemistry and immunology, which are within the skill of the art. Such techniques are explained fully in the literature for example in the following publications. See, e.g., Sambrook and Russell eds. MOLECULAR CLONING: A LABORATORY MANUAL, 3$^{rd}$ edition (2001); the series CURRENT PROTOCOLS IN MOLECULAR BIOLOGY (F. M. Ausubel et al. eds. (2007)); the series METHODS IN ENZYMOLOGY (Academic Press, Inc., N.Y.); PCR 1: A PRACTICAL APPROACH (M. MacPherson et al. IRL Press at Oxford University Press (1991)); PCR 2: A PRACTICAL APPROACH (M. J. MacPherson, B. D. Hames and G. R. Taylor eds. (1995)); ANTIBODIES, A LABORATORY MANUAL (Harlow and Lane eds. (1999)); CULTURE OF ANIMAL CELLS: A MANUAL OF BASIC TECHNIQUE (R. I. Freshney 5$^{th}$ edition (2005)); OLIGONUCLEOTIDE SYNTHESIS (M. J. Gait ed. (1984)); Mullis et al. U.S. Pat. No. 4,683,195; NUCLEIC ACID HYBRIDIZATION (B. D. Hames & S. J. Higgins eds. (1984)); NUCLEIC ACID HYBRIDIZATION (M. L. M. Anderson (1999)); TRANSCRIPTION AND TRANSLATION (B. D. Hames & S. J. Higgins-eds. (1984)); IMMOBILIZED CELLS AND ENZYMES (IRL Press (1986)); B. Perbal, A PRACTICAL GUIDE TO MOLECULAR CLONING (1984); GENE TRANSFER VECTORS FOR MAMMALIAN CELLS (J. H. Miller and M. P. Calos eds. (1987) Cold Spring Harbor Laboratory); GENE TRANSFER AND EXPRESSION IN MAMMALIAN CELLS (S. C. Makrides ed. (2003)) IMMUNOCHEMICAL METHODS IN CELL AND MOLECULAR BIOLOGY (Mayer and Walker, eds., Academic Press, London (1987)); WEIR'S HANDBOOK OF EXPERIMENTAL IMMUNOLOGY (L. A. Herzenberg et al. eds (1996)).

As used herein, certain terms may have the following defined meanings. As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively include additional steps and compositions of no significance (consisting essentially of) or alternatively, intending only the stated methods steps or compositions (consisting of).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

DEFINITIONS

The phrase "pyrimidine antimetabolite based therapy" refers to a therapeutic regime that comprises, or alternatively consists essentially of, or yet further consists of the administration of a compound that belongs to the family of chemotherapy drugs, such as, but not limited to 5-Fluorouracil, Capecitabine, or equivalents thereof which in one aspect is termed herein as "5-FU based adjuvant therapy." In another aspect, "pyrimidine antimetabolite based therapy" also refers to a therapeutic regime which also includes other compounds such as, but not limited to, Leucovorin, oxaliplatin, Irinotecan or equivalents thereof. In yet another aspect, "pyrimidine antimetabolite based therapy" also refers to a therapeutic regime that comprises surgery or radiation.

"5-FU based adjuvant therapy" refers to 5-FU or an equivalent thereof alone or alternatively the combination of such with other treatments, that include, but are not limited to radiation, methyl-CCNU, leucovorin, oxaliplatin, irinotecin, mitomycin, cytarabine, levamisole. Specific treatment adjuvant regimens are known in the art as FOLFOX, FOLFOX4, FOLFIRI, MOF (semustine (methyl-CCNU), vincrisine (Oncovin) and 5-FU). For a review of these therapies see Beaven and Goldberg (2006) Oncology 20(5):461-470. An example of such is an effective amount of 5-FU and Leucovorin. Other chemotherapeutics can be added, e.g., oxaliplatin or irinotecan.

"5-Fluorouracil" or "5-FU" belongs to the family of chemotherapy drugs called "pyrimidine antimetabolites." It is a pyrimidine based analog, which is transformed into different cytotoxic metabolites that are then incorporated into DNA and RNA thereby inducing cell cycle arrest and apoptosis. Similar to 5-FU, chemical equivalents are pyrimidine analogs which result in disruption of DNA replication. Chemical equivalents inhibit cell cycle progression at S phase resulting in the disruption of cell cycle and consequently apoptosis. Chemical equivalents are known in the art and are described, for example in Papamichael (2000) Stem Cells 18:166-175.

Equivalents to 5-FU include prodrugs, analogs and derivative thereof such as 5'-deoxy-5-fluorouridine (doxifluoroidine), 1-tetrahydrofuranyl-5-fluorouracil (ftorafur), Capecitabine (Xeloda), S-1 (MBMS-247616, consisting of tegafur and two modulators, a 5-chloro-2,4-dihydroxypyridine and potassium oxonate), ralititrexed (tomudex), nolatrexed (Thymitaq, AG337), LY231514 and ZD9331, as described for example in Papamicheal (1999) The Oncologist 4:478-487.

Capecitabine is marketed by Roche under the trade name Xeloda®. Capecitabine is an example of an equivalent of 5-FU. It is a prodrug of (5-FU) that is converted to its active form by the tumor-specific enzyme PynPase following a pathway of three enzymatic steps and two intermediary metabolites, 5'-deoxy-5-fluorocytidine (5'-DFCR) and 5'-deoxy-5-fluorouridine (5'-DFUR). Leucovorin or folinic acid, is the active form of folic acid in the body. It has been used as an antidote to protect normal cells from high doses of the anticancer drug methotrexate and to increase the antitumor effects of 5-fluorouracil (5-FU) and tegafururacil. It is also known as citrovorum factor and Wellcovorin. This compound has the chemical designation of L-Glutamic acid N[4[[(2-amino-5-formyl-1,4,5,6,7,8hexahydro-4-oxo6-pteridinyl) methyl]amino]benzoyl], calcium salt (1:1).

"Oxaliplatin" (Eloxatin®) is a platinum-based chemotherapy drug in the same family as cisplatin and carboplatin. It is typically administered in combination with 5-fluorouracil and Leucovorin in a combination known as FOLFOX for the treatment of colorectal cancer. Compared to cisplatin the two amine groups are replaced by cyclohexyldiamine for improved antitumor activity. The chlorine groups are replaced by the oxalato bidentate derived from oxalic acid in order to improve water solubility. Equivalents to oxaliplatin are known in the art and include without limitation cisplatin, carboplatin, aroplatin, lobaplatin, nedaplatin, and JM-216 (see McKeage et al. (1997) J. Clin. Oncol. 15:2691-2700 and in general, CHEMOTHERAPY FOR GYNECOLOGICAL NEOPLASM, CURRENT THERAPY AND NOVEL APPROACHES, in the Series Basic and Clinical Oncology, Angioli et al. Eds., 2004).

Irinotecan (CPT-11) is sold under the trade name of Camptosar®. It is a semi-synthetic analogue of the alkaloid camptothecin, which is activated by hydrolysis to SN-38 and targets topoisomerase 1. Chemical equivalents are those that inhibit the interaction of topoisomerase I and DNA to form a catalytically active topoisomerase I-DNA complex. Chemical equivalents inhibit cell cycle progression at G2-M phase resulting in the disruption of cell proliferation.

"FOLFOX" is an abbreviation for a type of combination therapy that can be used to treat colorectal cancer. FOLFOX includes 5-FU, oxaliplatin and Leucovorin. "XELOX" is an abbreviation for a type of combination therapy that can be used to treat metastatic colorectal cancer and colon cancer. XELOX includes Capecitabine and oxaliplatin. "FOLFIRI" is an abbreviation for a type of combination therapy that can be used to treat advanced colorectal cancer that has spread and can be used to treat other types of cancer. FOLFIRI includes 5-FU, Irinotecan and Leucovorin. Information regarding these combination therapies is available from the National Cancer Institute.

The phrase "first line," "second line," "third line," "fourth line" and "fifth line" refers to the order of treatment received by a patient. First line therapy regimens are treatments given first, whereas second, third, fourth or fifth line therapy are given after the first line therapy, after the second line therapy, after the third line therapy or after the fourth line therapy, respectively. The National Cancer Institute defines first line therapy as "The first treatment for a disease or condition. In patients with cancer, primary treatment can be surgery, chemotherapy, radiation therapy, or a combination of these therapies." First line therapy is also referred to those skilled in the art as primary therapy and primary treatment. Typically, a patient is given a subsequent chemotherapy regimen because the patient did not shown a positive clinical or sub-clinical response to the first line therapy or the first line therapy has stopped.

In one aspect, the "biological equivalent" means the ability of the antibody to selectively bind its epitope protein or fragment thereof as measured by ELISA or other suitable methods. Biologically equivalent antibodies include, but are not limited to, those antibodies, peptides, antibody fragments, antibody variant, antibody derivative and antibody mimetics that bind to the same epitope as the reference antibody. An example of an equivalent Bevacizumab antibody is one which binds to and inhibits the biologic activity of human vascular endothelial growth factor (VEGF).

In one aspect, the "chemical equivalent" means the ability of the chemical to selectively interact with its target protein, DNA, RNA or fragment thereof as measured by the inactivation of the target protein, incorporation of the chemical into the DNA or RNA or other suitable methods. Chemical equivalents include, but are not limited to, those agents with the same or similar biological activity and include, without limitation a pharmaceutically acceptable salt or mixtures thereof that interact with and/or inactivate the same target protein, DNA, or RNA as the reference chemical.

The term "allele," which is used interchangeably herein with "allelic variant" refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene. Alleles of a specific gene can differ from each other in a single nucleotide, or several nucleotides, and can include substitutions, deletions and insertions of nucleotides. An allele of a gene can also be a form of a gene containing a mutation.

The terms "protein," "polypeptide" and "peptide" are used interchangeably herein when referring to a gene product.

The term "recombinant protein" refers to a polypeptide which is produced by recombinant DNA techniques, wherein generally, DNA encoding the polypeptide is inserted into a suitable expression vector which is in turn used to transform a host cell to produce the heterologous protein.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

The term "allelic variant of a polymorphic region of the gene of interest" refers to a region of the gene of interest having one of a plurality of nucleotide sequences found in that region of the gene in other individuals.

As used herein, the term "gene of interest" intends the epidermal growth factor receptor (EGFR), also known as HER-1 or erbB-1.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The expression "amplification of polynucleotides" includes methods such as PCR, ligation amplification (or ligase chain reaction, LCR) and amplification methods. These methods are known and widely practiced in the art. See, e.g., U.S. Pat. Nos. 4,683,195 and 4,683,202 and Wu et al. (1989) Genomics 4:560-569 (for LCR). In general, the PCR procedure describes a method of gene amplification which is comprised of (i) sequence-specific hybridization of primers to specific genes within a DNA sample (or library), (ii) subsequent amplification involving multiple rounds of annealing, elongation, and denaturation using a DNA polymerase, and (iii) screening the PCR products for a band of the correct size. The primers used are oligonucleotides of sufficient length and appropriate sequence to provide initiation of polymerization, i.e. each primer is specifically designed to be complementary to each strand of the genomic locus to be amplified.

Reagents and hardware for conducting PCR are commercially available. Primers useful to amplify sequences from a particular gene region are preferably complementary to, and hybridize specifically to sequences in the target region or in its flanking regions. Nucleic acid sequences generated by amplification may be sequenced directly. Alternatively the amplified sequence(s) may be cloned prior to sequence analysis. A method for the direct cloning and sequence analysis of enzymatically amplified genomic segments is known in the art.

The term "encode" as it is applied to polynucleotides refers to a polynucleotide which is said to "encode" a polypeptide if, in its native state or when manipulated by methods well known to those skilled in the art, it can be transcribed and/or translated to produce the mRNA for the polypeptide and/or a fragment thereof. The antisense strand is the complement of such a nucleic acid, and the encoding sequence can be deduced therefrom.

The term "genotype" refers to the specific allelic composition of an entire cell or a certain gene and in some aspects a specific polymorphism associated with that gene, whereas the term "phenotype" refers to the detectable outward manifestations of a specific genotype.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

The term "a homolog of a nucleic acid" refers to a nucleic acid having a nucleotide sequence having a certain degree of homology with the nucleotide sequence of the nucleic acid or complement thereof. A homolog of a double stranded nucleic acid is intended to include nucleic acids having a nucleotide sequence which has a certain degree of homology with or with the complement thereof. In one aspect, homologs of nucleic acids are capable of hybridizing to the nucleic acid or complement thereof.

The term "interact" as used herein is meant to include detectable interactions between molecules, such as can be detected using, for example, a hybridization assay. The term interact is also meant to include "binding" interactions between molecules. Interactions may be, for example, protein-protein, protein-nucleic acid, protein-small molecule or small molecule-nucleic acid in nature.

The term "isolated" as used herein with respect to nucleic acids, such as DNA or RNA, refers to molecules separated from other DNAs or RNAs, respectively, that are present in the natural source of the macromolecule. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

The term "mismatches" refers to hybridized nucleic acid duplexes which are not 100% homologous. The lack of total homology may be due to deletions, insertions, inversions, substitutions or frameshift mutations.

As used herein, the term "nucleic acid" refers to polynucleotides such as deoxyribonucleic acid (DNA), and, where appropriate, ribonucleic acid (RNA). The term should also be understood to include, as equivalents, derivatives, variants and analogs of either RNA or DNA made from nucleotide analogs, and, as applicable to the embodiment being described, single (sense or antisense) and double-stranded polynucleotides. Deoxyribonucleotides include deoxyadenosine, deoxycytidine, deoxyguanosine, and deoxythymidine. For purposes of clarity, when referring herein to a nucleotide of a nucleic acid, which can be DNA or an RNA, the terms "adenosine," "cytidine," "guanosine," and "thymidine" are used. It is understood that if the nucleic acid is RNA, a nucleotide having a uracil base is uridine.

The terms "oligonucleotide" or "polynucleotide," or "portion," or "segment" thereof refer to a stretch of polynucleotide residues which is long enough to use in PCR or various hybridization procedures to identify or amplify identical or related parts of mRNA or DNA molecules. The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The term "polymorphism" refers to the coexistence of more than one form of a gene or portion thereof. A portion of a gene of which there are at least two different forms, i.e., two different nucleotide sequences, is referred to as a "polymorphic region of a gene." A polymorphic region can be a single nucleotide, the identity of which differs in different alleles.

A "polymorphic gene" refers to a gene having at least one polymorphic region.

As used herein, the term "gene" or "recombinant gene" refers to a nucleic acid molecule comprising an open reading frame and including at least one exon and (optionally) an intron sequence. The term "intron" refers to a DNA sequence present in a given gene which is spliced out during mRNA maturation.

When a genetic marker or polymorphism "is used as a basis" for selecting a patient for a treatment described herein, the genetic marker or polymorphism is measured before and/or during treatment, and the values obtained are used by a clinician in assessing any of the following: (a) probable or likely suitability of an individual to initially receive treatment(s); (b) probable or likely unsuitability of an individual to initially receive treatment(s); (c) responsiveness to treatment; (d) probable or likely suitability of an individual to continue to receive treatment(s); (e) probable or likely unsuitability of an individual to continue to receive treatment(s); (f) adjusting dosage; (g) predicting likelihood of clinical benefits; or (h) toxicity. As would be well understood by one in the art, measurement of the genetic marker or polymorphism in a clinical setting is a clear indication that this parameter was used as a basis for initiating, continuing, adjusting and/or ceasing administration of the treatments described herein.

The terms "treat," "treating" or "treatment" are used herein interchangeability and are intended to encompass curing as well as ameliorating at least one symptom of the condition or disease. For example, in the case of cancer, treatment includes a reduction in cachexia, increase in survival time, elongation in time to tumor progression, reduction in tumor mass, reduction in tumor burden and/or a prolongation in time to tumor metastasis, each as measured by standards set by the National Cancer Institute and the U.S. Food and Drug Administration for the approval of new drugs. See Johnson et al. (2003) J. Clin. Oncol. 21(7):1404-1411.

"An effective amount" intends to indicate the amount of a compound or agent administered or delivered to the patient which is most likely to result in the desired response to treatment. The amount is empirically determined by the patient's clinical parameters including, but not limited to the stage of disease, age, gender, histology, and likelihood for tumor recurrence.

The phrase "suitable for a therapy" shall mean that the patient is more likely than not to exhibit at least one of the described clinical parameters or treatment responses, identified herein, as compared to similarly situated patients without the polymorphism. Alternatively, "not suitable for therapy" indicates the patient is less likely than not to exhibit at least one of the described clinical parameters or treatment responses, identified herein, as compared to similarly situated patients without the polymorphism.

The term "clinical parameters" refers to a reduction or delay in recurrence of the cancer after the initial therapy, time to tumor recurrence (TTR), time to tumor progression (TTP), decrease in tumor load or size (tumor response or TR), progression free survival, increase median survival time (OS) or decrease metastases.

"Progression free survival" (PFS) indicates the length of time during and after treatment that the cancer does not grow. Progression-free survival includes the amount of time patients have experienced a complete response or a partial response, as well as the amount of time patients have experienced stable disease.

A "complete response" (CR) to a therapy defines patients with evaluable but non-measurable disease, whose tumor and all evidence of disease had disappeared.

A "partial response" (PR) to a therapy defines patients with anything less than complete response who were simply categorized as demonstrating partial response.

"Stable disease" (SD) indicates that the patient is stable.

"Non-response" (NR) to a therapy defines patients whose tumor or evidence of disease has remained constant or has progressed.

"Overall Survival" (OS) intends a prolongation in life expectancy as compared to naïve or untreated individuals or patients.

"Time to Tumor Recurrence" (TTR) is defined as the time from the date of diagnosis of the cancer to the date of first recurrence, death, or until last contact if the patient was free of any tumor recurrence at the time of last contact. If a patient had not recurred, then TTR was censored at the time of death or at the last follow-up.

DESCRIPTIVE EMBODIMENTS

In one embodiment, the inventions provides a method for identifying a female cancer patient suitable for a pyrimidine antimetabolite based therapy, comprising, or alternatively consisting essentially of, or alternatively consisting of determining a genotype of a cell or tissue sample isolated from the patient for at least one polymorphism of HER-1 (R497K) or EGFR intron 1 $(CA)_n$ repeat, wherein the genotype of one or more of Arg/Arg for HER-1 (R497K); or two alleles with a $(CA)_n$ repeat <20 (SEQ ID NO: 3) for EGFR intron 1 $(CA)_n$ repeat, identifies the patient as suitable for the therapy, or the genotype of one or more of Arg/Lys or Lys/Lys for HER-1 (R497K); or at least 1 allele with a $(CA)_n$ repeat ≥20 (SEQ ID NO: 4) for EGFR intron 1 $(CA)_n$ repeat, identifies the patient as not suitable for the therapy.

In another embodiment, the invention provides a method for identifying a female cancer patient suitable for a pyrimidine antimetabolite based therapy, comprising, or alternatively consisting essentially of, or alternatively consisting of determining a genotype of a cell or tissue sample isolated from the patient for both HER-1 (R497K) and EGFR intron 1 $(CA)_n$ repeat polymorphisms, wherein the genotype of: Arg/Arg for HER-1 (R497K) and two alleles with a $(CA)_n$ repeat <20 (SEQ ID NO: 3) for EGFR intron 1 $(CA)_n$ repeat; or Arg/Arg for HER-1 (R497K) and at least 1 allele with a $(CA)_n$ repeat ≥20 (SEQ ID NO: 4) for EGFR intron 1 $(CA)_n$ repeat; or Arg/Lys or Lys/Lys for HER-1 (R497K) and two alleles with a $(CA)_n$ repeat <20 (SEQ ID NO: 3) for EGFR intron 1 $(CA)_n$ repeat, identifies the patient as suitable for the therapy, or the genotype of: Arg/Lys or Lys/Lys for HER-1 (R497K); and at least 1 allele with a $(CA)_n$ repeat ≥20 (SEQ ID NO: 4) for EGFR intron 1 $(CA)_n$ repeat, identifies the patient as not suitable for the therapy.

In another embodiment, the invention provides a method for identifying a male cancer patient suitable for a pyrimidine antimetabolite based therapy, comprising, or alternatively consisting essentially of, or alternatively consisting of determining a genotype of a cell or tissue sample isolated from the patient for at least one polymorphism of HER-1 (R497K) or EGFR intron 1 $(CA)_n$ repeat, wherein the genotype of one or more of: Arg/Lys or Lys/Lys for HER-1 (R497K); or at least 1 allele with a $(CA)_n$ repeat ≥20 (SEQ ID NO: 4) for EGFR intron 1 $(CA)_n$ repeat, identifies the patient as suitable for the therapy, or the genotype of one or more of: Arg/Arg for HER-1 (R497K); or two alleles with a $(CA)_n$ repeat <20 (SEQ ID NO: 3) for EGFR intron 1 $(CA)_n$ repeat, identifies the patient as not suitable for the therapy.

In another embodiment, the invention provides a method for identifying a male cancer patient suitable for a pyrimidine antimetabolite based therapy, comprising, or alternatively consisting essentially of, or alternatively consisting of determining a genotype of a cell or tissue sample isolated from the patient for both HER-1 (R497K) and EGFR intron 1 $(CA)_n$ repeat polymorphisms, wherein the genotype of: Arg/Lys or Lys/Lys for HER-1 (R497K) and at least 1 allele with a $(CA)_n$ repeat ≥20 (SEQ ID NO: 4) for EGFR intron 1 $(CA)_n$ repeat; or Arg/Arg for HER-1 (R497K) and at least 1 allele with a $(CA)_n$ repeat ≥20 (SEQ ID NO: 4) for EGFR intron 1 $(CA)_n$ repeat; or Arg/Lys or Lys/Lys for HER-1 (R497K) and two alleles with a $(CA)_n$ repeat <20 (SEQ ID NO: 3) for EGFR intron 1 $(CA)_n$ repeat, identifies the patient as suitable for the therapy, or the genotype of: Arg/Arg for HER-1 (R497K); and two alleles with a $(CA)_n$ repeat <20 (SEQ ID NO: 3) for EGFR intron 1 $(CA)_n$ repeat, identifies the patient as not suitable for the therapy.

In one aspect of the above embodiments, the cancer patient is suffering from a cancer that is known to be treated or is suspected to be treated by a pyrimidine antimetabolite based therapy, such as, but not limited to 5-fluorouricil (5-FU), or alternatively a pyrimidine antimetabolite based therapy further comprising oxaliplatin or an equivalent thereof, or alternatively a pyrimidine antimetabolite based therapy further comprising Irinotecan or an equivalent thereof. In another aspect of the above embodiments, the cancer patient is suffering from a cancer of the type of the group: lung cancer, breast cancer, head and neck cancer, ovarian cancer, rectal cancer, colorectal cancer, colon cancer, metastatic colon cancer, advanced colon cancer, non-small cell lung cancer (NSCLC), advanced gastric cancer, metastatic gastric cancer, advanced hepatocarcinoma, metastatic liver cancer, metastatic intra-abdominal cancer, metastatic and non-metastatic bone cancer, metastatic and non-metastatic stomach cancer, metastatic and non-metastatic spleen cancer, metastatic and non-metastatic pancreatic cancer, metastatic and non-metastatic gallbladder cancer or other solid tumors. In yet another aspect, the cancer patient is suffering from colon cancer, metastatic colon cancer or advanced colon cancer.

In another aspect of the above embodiments, the pyrimidine antimetabolite based therapy comprises administration of 5-fluorouracil (5-FU) or an equivalent thereof. In a further aspect, the therapy comprises administration of irinotecan (CPT-11) or an equivalent thereof. In yet another further aspect, the therapy comprises administration of oxaliplatin or an equivalent thereof.

In another aspect of the above embodiments, the therapy is selected from the group consisting of first line therapy, second line therapy, third line therapy, fourth line therapy and fifth line therapy.

In yet another aspect of the above embodiments, the patient identified as suitable for the therapy is more likely to experience relatively longer overall survival than a patient who has the cancer but does not have the genotype and receives the therapy. In a further aspect, a patient having a genotype of a group that is likely to experience a relatively longer overall survival is a patient that is more likely to experience a relatively longer overall survival than patients suffering from a same cancer and receiving the therapy and not having a genotype of the group.

In yet another aspect of the above embodiments, the sample comprises a tumor cell, a normal cell adjacent to a tumor, a normal cell corresponding to a tumor tissue type, a blood cell, a peripheral blood lymphocyte or combinations thereof. As used herein, the term "normal cell corresponding to the tumor tissue type" refers to a normal cell from a same tissue type as the tumor tissue, such as a normal or non-cancerous lung cell from a patient having lung tumor or a normal colon or rectal cell from a patient having a colon cancer, colorectal cancer or rectal cancer.

In yet another aspect of the above embodiments, the sample is at least one of a fixed tissue, a frozen tissue, a biopsy tissue, a resection tissue, a microdissected tissue, a paraffin-embedded tissue or combinations thereof.

In yet another aspect of the above embodiments, the genotype is determined by a method comprising PCR, PCR-RFLP, sequencing or microarray.

In one aspect of each of the above methods, the patient is an animal patient. In another aspect, the patient is a mammalian, that includes without limitation simian, ovine, bovine, porcine murine or human patient. In another aspect, the patient is a human patient.

In another embodiment, the invention provides a method for treating a female cancer patient, comprising, or alternatively consisting essentially of, or alternatively consisting of: determining the genotype of a cell or tissue sample isolated from the patient for at least one polymorphism of HER-1 (R497K) or EGFR intron 1 $(CA)_n$ repeat; and administering to a patient, identified as having the genotype of Arg/Arg for HER-1 (R497K) or two alleles with a $(CA)_n$ repeat <20 (SEQ ID NO: 3) for EGFR intron 1 $(CA)_n$ repeat, a pyrimidine antimetabolite based treatment, thereby treating the patient.

In another embodiment, the invention provides a method for treating a female cancer patient, comprising, or alternatively consisting essentially of, or alternatively consisting of: determining the genotype of a cell or tissue sample isolated from the patient for a genotype of both HER-1 (R497K) and EGFR intron 1 $(CA)_n$ repeat polymorphisms; and administering to a patient, identified as having the genotype of Arg/Arg for HER-1 (R497K) and two alleles with a $(CA)_n$ repeat <20 (SEQ ID NO: 3) for EGFR intron 1 $(CA)_n$ repeat; or Arg/Arg for HER-1 (R497K) and at least 1 allele with a $(CA)_n$ repeat ≥20 (SEQ ID NO: 4) for EGFR intron 1 $(CA)_n$ repeat; or Arg/Lys or Lys/Lys for HER-1 (R497K) and two alleles with a $(CA)_n$ repeat <20 (SEQ ID NO: 3) for EGFR intron 1 $(CA)_n$ repeat, a pyrimidine antimetabolite based therapy, thereby treating the patient.

In another embodiment, the invention provides a method for treating a male cancer patient, comprising, or alternatively consisting essentially of, or alternatively consisting of: determining a genotype of a cell or tissue sample isolated from the patient for at least one polymorphism of HER-1 (R497K) or EGFR intron 1 $(CA)_n$ repeat; and administering to a patient having the genotype of Arg/Lys or Lys/Lys for HER-1 (R497K) or at least 1 allele with a $(CA)_n$ repeat ≥20 (SEQ ID NO: 4) for EGFR intron 1 $(CA)_n$ repeat a pyrimidine antimetabolite based treatment, thereby treating the patient.

In another embodiment, the invention provides a method for treating a male cancer patient, comprising, or alternatively consisting essentially of, or alternatively consisting of: determining a genotype of a cell or tissue sample isolated from the patient for a genotype of both HER-1 (R497K) and EGFR intron 1 (CA)$_n$ repeat polymorphisms; and administering to a patient, having the genotype of Arg/Lys or Lys/Lys for HER-1 (R497K) and at least 1 allele with a (CA)$_n$ repeat ≥20 (SEQ ID NO: 4) for EGFR intron 1 (CA)$_n$ repeat; or Arg/Arg for HER-1 (R497K) and at least 1 allele with a (CA)$_n$ repeat ≥20 (SEQ ID NO: 4) for EGFR intron 1 (CA)$_n$ repeat; or Arg/Lys or Lys/Lys for HER-1 (R497K) and two alleles with a (CA)$_n$ repeat <20 (SEQ ID NO: 3) for EGFR intron 1 (CA)$_n$ repeat, a pyrimidine antimetabolite based treatment, thereby treating the patient.

In one aspect of the above embodiments, the cancer patient is suffering from a cancer that is known to be treated or is suspected to be treated by a pyrimidine antimetabolite based therapy, such as, but not limited to 5-fluorouricil (5-FU), 5-FU based adjuvant therapy or alternatively a pyrimidine antimetabolite based therapy further comprising oxaliplatin or an equivalent thereof, or alternatively a pyrimidine antimetabolite based therapy further comprising Irinotecan or an equivalent thereof. In another aspect of the above embodiments, the cancer patient is suffering from a cancer of the type of the group: lung cancer, breast cancer, head and neck cancer, ovarian cancer, rectal cancer, colorectal cancer, colon cancer, metastatic colon cancer, advanced colon cancer, non-small cell lung cancer (NSCLC), advanced gastric cancer, metastatic gastric cancer, advanced hepatocarcinoma, metastatic and non-metastatic liver cancer, metastatic and non-metastatic intra-abdominal cancer, and non-metastatic bone cancer, and non-metastatic stomach cancer, and non-metastatic spleen cancer, and non-metastatic pancreatic cancer, and non-metastatic gallbladder cancer or other solid tumors. In yet another aspect, the cancer patient is suffering from colon cancer, metastatic colon cancer or advanced colon cancer.

In another aspect of the above embodiments, the pyrimidine antimetabolite based therapy comprises administration of 5-fluorouracil (5-FU) or an equivalent thereof or 5-FU based adjuvant therapy. In a further aspect, the therapy comprises administration of irinotecan (CPT-11) or an equivalent thereof. In yet another further aspect, the therapy comprises administration of oxaliplatin or an equivalent thereof.

In another aspect of the above embodiments, the therapy is selected from the group consisting of first line therapy, second line therapy, third line therapy, fourth line therapy and fifth line therapy.

In yet another aspect of the above embodiments, the sample comprises a tumor cell, a normal cell adjacent to a tumor, a normal cell corresponding to a tumor tissue type, a blood cell, a peripheral blood lymphocyte or combinations thereof.

In yet another aspect of the above embodiments, the sample is at least one of a fixed tissue, a frozen tissue, a biopsy tissue, a resection tissue, a microdissected tissue, a paraffin-embedded tissue or combinations thereof.

In yet another aspect of the above embodiments, the genotype is determined by a method comprising PCR, PCR-RFLP, sequencing or microarray.

In yet another aspect of the above embodiments, the patient is a human patient.

Methods to identify the polymorphisms described herein are known in the art. For example, the EGFR allele with the CA repeat polymorphism is identified and described in Buerger et al. (2000) Cancer Res. 60:854-857 and Gebhardt et al. (1999) J. Biol. Chem. 274:13176-13180. The HER-1 (R497K) polymorphism is identified and described in Moriai et al. (1993) Biochem. Biophys. Res. Commun. 191(3):1034-1039.

Diagnostic Methods

The invention further provides diagnostic methods, which are based, at least in part, on determination of the identity of the polymorphic region of the alleles identified in Table 1 above.

For example, information obtained using the diagnostic assays described herein is useful for determining if a subject is suitable for cancer treatment of a given type. Based on the prognostic information, a doctor can recommend a therapeutic protocol, useful for reducing the malignant mass or tumor in the patient or treat cancer in the individual.

Determining whether a subject is suitable or not suitable for cancer treatment of a given type, alternatively, can be expressed as identifying a subject suitable for the cancer treatment or identifying a subject not suitable for the cancer treatment of the given type.

It is to be understood that information obtained using the diagnostic assays described herein may be used alone or in combination with other information, such as, but not limited to, genotypes or expression levels of other genes, clinical chemical parameters, histopathological parameters, or age, gender and weight of the subject. When used alone, the information obtained using the diagnostic assays described herein is useful in determining or identifying the clinical outcome of a treatment, selecting a patient for a treatment, or treating a patient. When used in combination with other information, on the other hand, the information obtained using the diagnostic assays described herein is useful in aiding in the determination or identification of clinical outcome of a treatment, aiding in the selection of a patient for a treatment, or aiding in the treatment of a patient. In a particular aspect, the genotypes or expression levels of one or more genes as disclosed herein are used in a panel of genes, each of which contributes to the final diagnosis, prognosis or treatment.

In addition, knowledge of the identity of a particular allele in an individual (the gene profile) allows customization of therapy for a particular disease to the individual's genetic profile, the goal of "pharmacogenomics". For example, an individual's genetic profile can enable a doctor: 1) to more effectively prescribe a drug that will address the molecular basis of the disease or condition; 2) to better determine the appropriate dosage of a particular drug and 3) to identify novel targets for drug development. Expression patterns of individual patients can then be compared to the expression profile of the disease to determine the appropriate drug and dose to administer to the patient.

The ability to target populations expected to show the highest clinical benefit, based on the normal or disease genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling.

Detection of point mutations or additional base pair repeats can be accomplished by molecular cloning of the specified allele and subsequent sequencing of that allele using techniques known in the art, in some aspects, after isolation of a suitable nucleic acid sample using methods known in the art. Alternatively, the gene sequences can be amplified directly from a genomic DNA preparation from the tumor tissue using PCR, and the sequence composition is determined from the amplified product. As described more fully below, numerous methods are available for isolating and analyzing a subject's DNA for mutations at a given genetic locus such as the gene of interest.

A detection method is allele specific hybridization using probes overlapping the polymorphic site and having about 5, or alternatively 10, or alternatively 20, or alternatively 25, or alternatively 30 nucleotides around the polymorphic region. In another embodiment of the invention, several probes capable of hybridizing specifically to the allelic variant are attached to a solid phase support, e.g., a "chip". Oligonucleotides can be bound to a solid support by a variety of processes, including lithography. For example a chip can hold up to 250,000 oligonucleotides (GeneChip, Affymetrix). Mutation detection analysis using these chips comprising oligonucleotides, also termed "DNA probe arrays" is described e.g., in Cronin et al. (1996) Human Mutation 7:244.

In other detection methods, it is necessary to first amplify at least a portion of the gene of interest prior to identifying the allelic variant. Amplification can be performed, e.g., by PCR and/or LCR, according to methods known in the art. In one embodiment, genomic DNA of a cell is exposed to two PCR primers and amplification for a number of cycles sufficient to produce the required amount of amplified DNA.

Alternative amplification methods include: self sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), or any other nucleic acid amplification method, followed by the detection of the amplified molecules using techniques known to those of skill in the art. These detection schemes are useful for the detection of nucleic acid molecules if such molecules are present in very low numbers.

In one embodiment, any of a variety of sequencing reactions known in the art can be used to directly sequence at least a portion of the gene of interest and detect allelic variants, e.g., mutations, by comparing the sequence of the sample sequence with the corresponding wild-type (control) sequence. Exemplary sequencing reactions include those based on techniques developed by Maxam and Gilbert (1997) Proc. Natl. Acad. Sci. USA 74:560) or Sanger et al. (1977) Proc. Nat. Acad. Sci. 74:5463). It is also contemplated that any of a variety of automated sequencing procedures can be utilized when performing the subject assays (Naeve et al. (1995) Biotechniques 19:448), including sequencing by mass spectrometry (see, for example, U.S. Pat. No. 5,547,835 and International Patent Application Publication Number WO 94/16101, entitled DNA Sequencing by Mass Spectrometry by Koster; U.S. Pat. No. 5,547,835 and international patent application Publication Number WO 94/21822 entitled "DNA Sequencing by Mass Spectrometry Via Exonuclease Degradation" by Koster; U.S. Pat. No. 5,605,798 and International Patent Application No. PCT/US96/03651 entitled DNA Diagnostics Based on Mass Spectrometry by Koster; Cohen et al. (1996) Adv. Chromat. 36:127-162; and Griffin et al. (1993) Appl. Biochem. Bio. 38:147-159). It will be evident to one skilled in the art that, for certain embodiments, the occurrence of only one, two or three of the nucleic acid bases need be determined in the sequencing reaction. For instance, A-track or the like, e.g., where only one nucleotide is detected, can be carried out.

Yet other sequencing methods are disclosed, e.g., in U.S. Pat. No. 5,580,732 entitled "Method of DNA Sequencing Employing A Mixed DNA-Polymer Chain Probe" and U.S. Pat. No. 5,571,676 entitled "Method For Mismatch-Directed In vitro DNA Sequencing."

In some cases, the presence of the specific allele in DNA from a subject can be shown by restriction enzyme analysis. For example, the specific nucleotide polymorphism can result in a nucleotide sequence comprising a restriction site which is absent from the nucleotide sequence of another allelic variant.

In a further embodiment, protection from cleavage agents (such as a nuclease, hydroxylamine or osmium tetroxide and with piperidine) can be used to detect mismatched bases in RNA/RNA DNA/DNA, or RNA/DNA heteroduplexes (see, e.g., Myers et al. (1985) Science 230:1242). In general, the technique of "mismatch cleavage" starts by providing heteroduplexes formed by hybridizing a control nucleic acid, which is optionally labeled, e.g., RNA or DNA, comprising a nucleotide sequence of the allelic variant of the gene of interest with a sample nucleic acid, e.g., RNA or DNA, obtained from a tissue sample. The double-stranded duplexes are treated with an agent which cleaves single-stranded regions of the duplex such as duplexes formed based on basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine whether the control and sample nucleic acids have an identical nucleotide sequence or in which nucleotides they are different. See, for example, U.S. Pat. No. 6,455,249; Cotton et al. (1988) Proc. Natl. Acad. Sci. USA 85:4397; Saleeba et al. (1992) Methods Enzy. 217:286-295. In another embodiment, the control or sample nucleic acid is labeled for detection.

In other embodiments, alterations in electrophoretic mobility are used to identify the particular allelic variant. For example, single strand conformation polymorphism (SSCP) may be used to detect differences in electrophoretic mobility between mutant and wild type nucleic acids (Orita et al. (1989) Proc. Natl. Acad. Sci. USA 86:2766; Cotton (1993) Mutat. Res. 285:125-144 and Hayashi (1992) Genet. Anal. Tech. Appl. 9:73-79). Single-stranded DNA fragments of sample and control nucleic acids are denatured and allowed to renature. The secondary structure of single-stranded nucleic acids varies according to sequence. The resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In another preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment, the identity of the allelic variant is obtained by analyzing the movement of a nucleic acid comprising the polymorphic region in polyacrylamide gels containing a gradient of denaturant, which is assayed using denaturing gradient gel electrophoresis (DGGE) (Myers et al. (1985) Nature 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner (1987) Biophys. Chem. 265:1275).

Examples of techniques for detecting differences of at least one nucleotide between 2 nucleic acids include, but are not limited to, selective oligonucleotide hybridization, selective amplification, or selective primer extension. For example, oligonucleotide probes may be prepared in which the known polymorphic nucleotide is placed centrally (allele-specific probes) and then hybridized to target DNA under conditions which permit hybridization only if a perfect match is found (Saiki et al. (1986) Nature 324:163); Saiki et al. (1989) Proc. Natl. Acad. Sci. USA 86:6230 and Wallace et al. (1979) Nucl. Acids Res. 6:3543). Such allele specific oligonucleotide hybridization techniques may be used for the detection of the nucleotide changes in the polymorphic region of the gene of interest. For example, oligonucleotides having the nucleotide sequence of the specific allelic variant are attached to a hybridizing membrane and this membrane is then hybridized with labeled sample nucleic acid. Analysis of the hybridization signal will then reveal the identity of the nucleotides of the sample nucleic acid.

Alternatively, allele specific amplification technology which depends on selective PCR amplification may be used in conjunction with the instant invention. Oligonucleotides used as primers for specific amplification may carry the allelic variant of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238 and Newton et al. (1989) Nucl. Acids Res. 17:2503). This technique is also termed "PROBE" for Probe Oligo Base Extension. In addition it may be desirable to introduce a novel restriction site in the region of the mutation to create cleavage-based detection (Gasparini et al. (1992) Mol. Cell. Probes 6:1).

In another embodiment, identification of the allelic variant is carried out using an oligonucleotide ligation assay (OLA), as described, e.g., in U.S. Pat. No. 4,998,617 and in Landegren et al. (1988) Science 241:1077-1080. The OLA protocol uses two oligonucleotides which are designed to be capable of hybridizing to abutting sequences of a single strand of a target. One of the oligonucleotides is linked to a separation marker, e.g., biotinylated, and the other is detectably labeled. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson et al. have described a nucleic acid detection assay that combines attributes of PCR and OLA (Nickerson et al. (1990) Proc. Natl. Acad. Sci, (U.S.A.) 87:8923-8927). In this method, PCR is used to achieve the exponential amplification of target DNA, which is then detected using OLA.

Several techniques based on this OLA method have been developed and can be used to detect the specific allelic variant of the polymorphic region of the gene of interest. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. (1996) Nucleic Acids Res. 24:3728, OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

In one embodiment, the single base polymorphism can be detected by using a specialized exonuclease-resistant nucleotide, as disclosed, e.g., in Mundy (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of the polymorphic site. Cohen et al. (French Patent 2,650, 840; PCT Publication No. WO 91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA™ is described by Goelet et al. (PCT Publication No. 92/15712). This method uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al. (French Patent 2,650,840; PCT Publication No. WO 91/02087) the method of Goelet et al. supra, is preferably a heterogeneous phase assay, in which the primer or the target molecule is immobilized to a solid phase.

Recently, several primer-guided nucleotide incorporation procedures for assaying polymorphic sites in DNA have been described (Komher et al. (1989) Nucl. Acids. Res. 17:7779-7784; Sokolov (1990) Nucl. Acids Res. 18:3671; Syvanen et al. (1990) Genomics 8:684-692; Kuppuswamy et al. (1991) Proc. Natl. Acad. Sci. (U.S.A.) 88:1143-1147; Prezant et al. (1992) Hum. Mutat. 1:159-164; Ugozzoli et al. (1992) GATA 9:107-112; Nyren et al. (1993) Anal. Biochem. 208:171-175). These methods differ from GBA™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen et al. (1993) Amer. J. Hum. Genet. 52:46-59).

If the polymorphic region is located in the coding region of the gene of interest, methods other than those described above can be used for determining the identity of the allelic variant. For example, identification of the allelic variant, which encodes a mutated signal peptide, can be performed by using an antibody specifically recognizing the mutant protein in, e.g., immunohistochemistry or immunoprecipitation. Antibodies to the wild-type or signal peptide mutated forms of the signal peptide proteins can be prepared according to methods known in the art.

Often a solid phase support or carrier is used as a support capable of binding of a primer, probe, polynucleotide, an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. or alternatively polystyrene beads. Those skilled in the art will know many other suitable carriers for binding antibody or antigen, or will be able to ascertain the same by use of routine experimentation.

Moreover, it will be understood that any of the above methods for detecting alterations in a gene or gene product or polymorphic variants can be used to monitor the course of treatment or therapy.

The methods described herein may be performed, for example, by utilizing pre-packaged diagnostic kits, such as those described below, comprising at least one probe or primer nucleic acid described herein, which may be conveniently used, e.g., to determine whether a subject is likely responsive to the therapy as described herein or has or is at risk of developing disease such as colorectal cancer.

In one particular aspect, the invention provides a prognostic panel of genetic markers comprising, or alternatively consisting essentially of, or yet further consisting of, a primer or nucleic acid probe that identifies the genotype of a patient sample for at least one or more genetic polymorphism of the group: HER-1 (R497K) or EGFR intron 1 $(CA)_n$ repeat. In another embodiment, the panel comprises probes or primers are attached to a microarray specific to identify the polymorphisms. These may in one aspect be detectably labeled.

In one embodiment, the panel determines whether a gastrointestinal cancer or lung cancer patient in need thereof panel determines whether a cancer patient in need thereof is suitable for a pyrmidine antimetabolite based therapy. In one aspect, the pyrimidine antimetabolite based therapy comprises, or alternatively consists essentially of, or yet further consists of, administration of 5-fluorouracil (5-FU) or an equivalent thereof or 5-FU based adjuvant therapy. In a further aspect, the therapy further comprises, or alternatively consists essentially of, or yet further consists of, administration of irinotecan (CPT-11) or an equivalent thereof. In yet a further aspect, the therapy further comprises, or alternatively consists essentially of, or yet further consists of, administration of oxaliplatin or an equivalent thereof.

Sample nucleic acid for use in the above-described diagnostic and prognostic methods can be obtained from any suitable cell type or tissue of a subject. For example, a subject's bodily fluid (e.g. blood) can be obtained by known techniques (e.g., venipuncture). Alternatively, nucleic acid tests can be performed on dry samples (e.g., hair or skin). Fetal nucleic acid samples can be obtained from maternal blood as described in International Patent Publication No. WO 91/07660 to Bianchi. Alternatively, amniocytes or chorionic villi can be obtained for performing prenatal testing.

Diagnostic procedures can also be performed in situ directly upon tissue sections (fixed and/or frozen) of patient tissue obtained from biopsies or resections, such that no nucleic acid purification is necessary. Nucleic acid reagents can be used as probes and/or primers for such in situ procedures (see, for example, Nuovo (1992) PCR IN SITU HYBRIDIZATION: PROTOCOLS AND APPLICATIONS, Raven Press, NY).

In addition to methods which focus primarily on the detection of one nucleic acid sequence, profiles can also be assessed in such detection schemes. Fingerprint profiles can be generated, for example, by utilizing a differential display procedure, Northern analysis and/or RT-PCR.

The invention further provides methods for detecting the single nucleotide polymorphism in the gene of interest. Because single nucleotide polymorphisms constitute sites of variation flanked by regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms.

In one embodiment, the single base polymorphism can be detected by using a specialized exonuclease-resistant nucleotide, as disclosed, e.g., in Mundy (U.S. Pat. No. 4,656,127). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a finding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of the polymorphic site. Cohen et al. (French Patent 2,650, 840; PCT Publication No. WO 91/02087). As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

Antibodies directed against wild type or mutant peptides encoded by the allelic variants of the gene of interest may also be used in disease diagnostics and prognostics. Such diagnostic methods, may be used to detect abnormalities in the level of expression of the peptide, or abnormalities in the structure and/or tissue, cellular, or subcellular location of the peptide. Protein from the tissue or cell type to be analyzed may easily be detected or isolated using techniques which are well known to one of skill in the art, including but not limited to Western blot analysis. For a detailed explanation of methods for carrying out Western blot analysis, see Sambrook and Russell (2000) supra. The protein detection and isolation methods employed herein can also be such as those described in Harlow and Lane, (1999) supra. This can be accomplished, for example, by immunofluorescence techniques employing a fluorescently labeled antibody (see below) coupled with light microscopic, flow cytometric, or fluorimetric detection. The antibodies (or fragments thereof) useful in the present invention may, additionally, be employed histologically, as in immunofluorescence or immunoelectron microscopy, for in situ detection of the peptides or their allelic variants. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the subject polypeptide, but also its distribution in the examined tissue. Using the present invention, one of ordinary skill will readily perceive that any of a wide variety of histological methods (such as staining procedures) can be modified in order to achieve such in situ detection.

The invention described herein relates to methods and compositions for determining and identifying the allele present at the gene of interest's locus. This information is useful to diagnose and prognose disease progression as well as select the most effective treatment among treatment options. Probes can be used to directly determine the genotype of the sample or can be used simultaneously with or subsequent to amplification. The term "probes" includes naturally occurring or recombinant single- or double-stranded nucleic acids or chemically synthesized nucleic acids. They may be labeled by nick translation, Klenow fill-in reaction, PCR or other methods known in the art. Probes of the present invention, their preparation and/or labeling are described in Sambrook and Russell (2000) supra. A probe can be a polynucleotide of any length suitable for selective hybridization to a nucleic acid containing a polymorphic region of the invention. Length of the probe used will depend, in part, on the nature of the assay used and the hybridization conditions employed.

In one embodiment of the invention, probes are labeled with two fluorescent dye molecules to form so-called "molecular beacons" (Tyagi and Kramer (1996) Nat. Biotechnol. 14:303-8). Such molecular beacons signal binding to a complementary nucleic acid sequence through relief of intramolecular fluorescence quenching between dyes bound to opposing ends on an oligonucleotide probe. The use of molecular beacons for genotyping has been described (Kostrikis (1998) Science 279:1228-9) as has the use of multiple beacons simultaneously (Marras (1999) Genet. Anal. 14:151-6). A quenching molecule is useful with a particular fluorophore if it has sufficient spectral overlap to substantially inhibit fluorescence of the fluorophore when the two are held proximal to one another, such as in a molecular beacon, or when attached to the ends of an oligonucleotide probe from about 1 to about 25 nucleotides.

Labeled probes also can be used in conjunction with amplification of a polymorphism. (Holland et al. (1991) Proc. Natl. Acad. Sci. 88:7276-7280). U.S. Pat. No. 5,210,015 by Gelfand et al. describe fluorescence-based approaches to provide real time measurements of amplification products during PCR. Such approaches have either employed intercalating dyes (such as ethidium bromide) to indicate the amount of double-stranded DNA present, or they have employed probes containing fluorescence-quencher pairs (also referred to as the "Taq-Man" approach) where the probe is cleaved during amplification to release a fluorescent molecule whose concentration is proportional to the amount of double-stranded DNA present. During amplification, the probe is digested by the nuclease activity of a polymerase when hybridized to the target sequence to cause the fluorescent molecule to be separated from the quencher molecule, thereby causing fluorescence from the reporter molecule to appear. The Taq-Man approach uses a probe containing a reporter molecule-quencher molecule pair that specifically anneals to a region of a target polynucleotide containing the polymorphism.

Probes can be affixed to surfaces for use as "gene chips" or "microarray." Such gene chips or microarrays can be used to detect genetic variations by a number of techniques known to one of skill in the art. In one technique, oligonucleotides are arrayed on a gene chip for determining the DNA sequence of a by the sequencing by hybridization approach, such as that outlined in U.S. Pat. Nos. 6,025,136 and 6,018,041. The probes of the invention also can be used for fluorescent detection of a genetic sequence. Such techniques have been described, for example, in U.S. Pat. Nos. 5,968,740 and 5,858,659. A probe also can be affixed to an electrode surface for the electrochemical detection of nucleic acid sequences such as described by Kayem et al. U.S. Pat. No. 5,952,172 and by Kelley et al. (1999) Nucleic Acids Res. 27:4830-4837.

Various "gene chips" or "microarry" and similar technologies are known in the art. Examples of such include, but are not limited to LabCard (ACLARA Bio Sciences Inc.); GeneChip (Affymetric, Inc); LabChip (Caliper Technologies Corp); a low-density array with electrochemical sensing (Clinical Micro Sensors); LabCD System (Gamera Bioscience Corp.); Omni Grid (Gene Machines); Q Array (Genetix Ltd.); a high-throughput, automated mass spectrometry systems with liquid-phase expression technology (Gene Trace Systems, Inc.); a thermal jet spotting system (Hewlett Packard Company); Hyseq HyChip (Hyseq, Inc.); BeadArray (Illumina, Inc.); GEM (Incyte Microarray Systems); a high-throughput microarrying system that can dispense from 12 to 64 spots onto multiple glass slides (Intelligent Bio-Instruments); Molecular Biology Workstation and NanoChip (Nanogen, a microfluidic glass chip (Orchid Biosciences, Inc.); BioChip Arrayer with four PiezoTip piezoelectric drop-on-demand tips (Packard Instruments, Inc.); FlexJet (Rosetta Inpharmatic, Inc.); MALDI-TOF mass spectrometer (Sequnome); ChipMaker 2 and ChipMaker 3 (TeleChem International, Inc.); and GenoSensor (Vysis, Inc.) as identified and described in Heller (2002) Annu. Rev. Biomed. Eng. 4:129-153. Examples of "gene chips" or a "microarray" are also described in US Patent Publ. Nos.: 2007-0111322, 2007-0099198, 2007-0084997, 2007-0059769 and 2007-0059765 and U.S. Pat. Nos. 7,138,506, 7,070,740, and 6,989,267.

In one aspect, "gene chips" or "microarrays" containing probes or primers described herein, alone or in combination, are prepared. A suitable sample is obtained from the patient extraction of genomic DNA, RNA, or any combination thereof and amplified if necessary. The DNA or RNA sample is contacted to the gene chip or microarray panel under conditions suitable for hybridization of the gene(s) of interest to the probe(s) or primer(s) contained on the gene chip or microarray. The probes or primers may be detectably labeled thereby identifying the polymorphism in the gene(s) of interest. Alternatively, a chemical or biological reaction may be used to identify the probes or primers which hybridized with the DNA or RNA of the gene(s) of interest. The genotypes of the patient is then determined with the aid of the aforementioned apparatus and methods.

Nucleic Acids

In one aspect, the nucleic acid sequences of the gene's allelic variants, or portions thereof, can be the basis for probes or primers, e.g., in methods for determining the identity of the allelic variant of a polymorphic region of interest, e.g., HER-1 (R497K) or EGFR intron 1 $(CA)_n$ repeat. Thus, they can be used in the methods of the invention to determine which therapy is most likely to treat an individual's cancer.

The methods of the invention can use nucleic acids isolated from vertebrates. In one aspect, the vertebrate nucleic acids are mammalian nucleic acids. In a further aspect, the nucleic acids used in the methods of the invention are human nucleic acids.

Primers for use in the methods of the invention are nucleic acids which hybridize to a nucleic acid sequence which is adjacent to the region of interest or which covers the region of interest and is extended. A primer can be used alone in a detection method, or a primer can be used together with at least one other primer or probe in a detection method. Primers can also be used to amplify at least a portion of a nucleic acid. Probes for use in the methods of the invention are nucleic acids which hybridize to the region of interest and which are not further extended. For example, a probe is a nucleic acid which hybridizes to the polymorphic region of the gene of interest, and which by hybridization or absence of hybridization to the DNA of a subject will be indicative of the identity of the allelic variant of the polymorphic region of the gene of interest.

In one embodiment, primers comprise a nucleotide sequence which comprises a region having a nucleotide sequence which hybridizes under stringent conditions to about: 6, or alternatively 8, or alternatively 10, or alternatively 12, or alternatively 25, or alternatively 30, or alternatively 40, or alternatively 50, or alternatively 75 consecutive nucleotides of the gene of interest.

Primers can be complementary to nucleotide sequences located close to each other or further apart, depending on the use of the amplified DNA. For example, primers can be chosen such that they amplify DNA fragments of at least about 10 nucleotides or as much as several kilobases. Preferably, the primers of the invention will hybridize selectively to nucleotide sequences located about 150 to about 350 nucleotides apart.

For amplifying at least a portion of a nucleic acid, a forward primer (i.e., 5' primer) and a reverse primer (i.e., 3' primer) will preferably be used. Forward and reverse primers hybridize to complementary strands of a double stranded nucleic acid, such that upon extension from each primer, a double stranded nucleic acid is amplified.

Yet other preferred primers of the invention are nucleic acids which are capable of selectively hybridizing to an allelic variant of a polymorphic region of the gene of interest. Thus, such primers can be specific for the gene of interest sequence, so long as they have a nucleotide sequence which is capable of hybridizing to the gene of interest.

The probe or primer may further comprises a label attached thereto, which, e.g., is capable of being detected, e.g. the label group is selected from amongst radioisotopes, fluorescent compounds, enzymes, and enzyme co-factors.

Additionally, the isolated nucleic acids used as probes or primers may be modified to become more stable. Exemplary nucleic acid molecules which are modified include phosphoramidate, phosphothioate and methylphosphonate analogs of DNA (see also U.S. Pat. Nos. 5,176,996; 5,264,564 and 5,256,775).

The nucleic acids used in the methods of the invention can also be modified at the base moiety, sugar moiety, or phosphate backbone, for example, to improve stability of the molecule. The nucleic acids, e.g., probes or primers, may include other appended groups such as peptides (e.g., for targeting host cell receptors in vivo), or agents facilitating transport across the cell membrane. See, e.g., Letsinger et al. (1989) Proc. Natl. Acad. Sci. U.S.A. 86:6553-6556; Lemaitre et al. (1987) Proc. Natl. Acad. Sci. 84:648-652; and PCT Publication No. WO 88/09810, published Dec. 15, 1988), hybridization-triggered cleavage agents, (see, e.g., Krol et al. (1988) BioTechniques 6:958-976) or intercalating agents (see, e.g., Zon (1988) Pharm. Res. 5:539-549. To this end, the nucleic acid used in the methods of the invention may be conjugated to another molecule, e.g., a peptide, hybridization triggered cross-linking agent, transport agent, hybridization-triggered cleavage agent, etc.

The isolated nucleic acids used in the methods of the invention can also comprise at least one modified sugar moiety selected from the group including but not limited to arabinose, 2-fluoroarabinose, xylulose, and hexose or, alternatively, comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

The nucleic acids, or fragments thereof, to be used in the methods of the invention can be prepared according to methods known in the art and described, e.g., in Sambrook and Russell (2000) supra. For example, discrete fragments of the DNA can be prepared and cloned using restriction enzymes. Alternatively, discrete fragments can be prepared using the Polymerase Chain Reaction (PCR) using primers having an appropriate sequence under the manufacturer's conditions, (described above).

Oligonucleotides can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988) Nucl. Acids Res. 16:3209, methylphosphonate oligonucleotides can be prepared by use of controlled pore glass polymer supports. Sarin et al. (1988) Proc. Natl. Acad. Sci. U.S.A. 85:7448-7451.

Methods of Treatment

The invention further provides methods of treating subjects having cancer as identified above, which includes for example, rectal cancer, colorectal cancer, (including metastatic CRC), colon cancer (metastatic or advanced colon cancer), gastric cancer (metastatic or advanced gastric cancer), lung cancer (including non-small cell lung cancer) breast cancer, head and neck cancer, ovarian cancer advanced hepatocarcinoma metastatic and non-metastatic liver cancer, metastatic and non-metastatic intra-abdominal cancer, and non-metastatic bone cancer, and non-metastatic stomach cancer, and non-metastatic spleen cancer, and non-metastatic pancreatic cancer, and non-metastatic gallbladder cancer and other solid tumors. In one embodiment, the method comprises, or alternatively consists essentially of or yet further consists of: (a) determining the genotype of a cell or tissue sample'isolated from the patient for the allelic variant as identified herein; and (b) administering to the patient an effective amount of a compound or therapy (e.g., a pyrimidine antimetabolite based therapy). This therapy can be combined with other suitable therapies or treatments such as radiation therapy or surgery.

In certain embodiments, an effective amount of Fluorouracil (5-FU) or a chemical equivalent or 5-FU based adjuvant therapy and an efficacy enhancing agent are administered to the patient. In general, compositions comprising these compounds can be prepared in accordance with known formulation techniques to provide a composition suitable for oral, topical, transdermal, rectal, inhalation, or parenteral (intravenous, intramuscular, or intraperitoneal) administration, and the like. In general the dosing, route of administration, and administration schedule of this compound is well know in the art. Examples of such can be found in, but are not limited to Gramont et al. (2000) J. Clin. Oncol. 18(16):2938-2947 and Cassidy et al. (2004) J. Clin. Oncol. 22(11):2084-2091.

Fluorouracil (5-FU) or a chemical equivalent alone or with an adjuvant is administered in a therapeutically effective amount sufficient to treat cancer in a subject and may contain from about 1.0 to 2000 mg/m$^2$/day of compound, for example about 1, 5, 10, 15, 20, 25, 50, 75, 100, 125, 150, 175, 200, 225, 250, 275, 300, 325, 350, 375, 400, 425, 450, 475, 500, 550, 600, 650, 700, 750, 800, 850, 900, 950, 1000, 1100, 1200, 1300, 1400, 1500, 1600, 1700, 1800, 1900, to 2000 mg/m$^2$.

Fluorouracil (5-FU) or a chemical equivalent alone or an adjuvant may be administered parenterally, e.g., intravenously, intramuscularly, intravenously, subcutaneously, or interperitonically. The carrier or excipient or excipient mixture can be a solvent or a dispersive medium containing, for example, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Except insofar as any conventional media or agent is incompatible with the active ingredient, use in therapeutic compositions is contemplated. Moreover, other or supplementary active ingredients can also be incorporated into the final composition.

Solutions of Fluorouracil (5-FU) or a chemical equivalent and an adjuvant may be prepared in suitable diluents such as water, ethanol, glycerol, liquid polyethylene glycol(s), various oils, and/or mixtures thereof, and others known to those skilled in the art.

The pharmaceutical forms of Fluorouracil (5-FU) or a chemical equivalent suitable or an adjuvant for injectable use include sterile solutions, dispersions, emulsions, and sterile powders. The final form must be stable under conditions of manufacture and storage. Furthermore, the final pharmaceutical form must be protected against contamination and must, therefore, be able to inhibit the growth of microorganisms such as bacteria or fungi. A single intravenous or intraperitoneal dose can be administered. Alternatively, a slow long term infusion or multiple short term daily infusions may be utilized, typically lasting from 1 to 8 days. Alternate day or dosing once every several days may also be utilized.

Sterile, injectable solutions are prepared by incorporating a compound in the required amount into one or more appropriate solvents to which other ingredients, listed above or known to those skilled in the art, may be added as required. Sterile injectable solutions are prepared by incorporating the compound in the required amount in the appropriate solvent with various other ingredients as required. Sterilizing procedures, such as filtration, then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

In all cases the final form, as noted, must be sterile and must also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

Prevention or inhibition of growth of microorganisms may be achieved through the addition of one or more antimicrobial agents such as chlorobutanol, ascorbic acid, parabens, thermerosal, or the like. It may also be preferable to include agents that alter the tonicity such as sugars or salts.

In one aspect of the invention, a chemical equivalent of 5-FU (a pyrimidine anti-metabolite) selected from the group of, but not limited to, Cytarabine and Gemcitabine as described in Maring et al. (2005) Pharmacogenomics J. 5(4): 226-243; and Floxuridine as described in Mayer (1992) Cancer 70(5 Suppl):1414-1424, can be used to treat patients identified as having the appropriate genetic polymorphisms.

In certain embodiments, an effective amount of Leucovorin (Folinic acid) or a chemical equivalent as an adjuvant is administered to the patient for the purpose of enhancing the cytotoxic effects of 5-FU or a chemical equivalent. In general, compositions comprising these compounds can be prepared in accordance with known formulation techniques to provide a composition suitable for oral, topical, transdermal, rectal, inhalation, or parenteral (intravenous, intramuscular, or intraperitoneal) administration, and the like. In general the dosing, route of administration, and administration schedule of this compound is well know in the art. Examples of such can be found in, but are not limited to Gramont et al. (2000) J. Clin. Oncol. 18(16):2938-2947 and Cassidy et al. (2004) J. Clin. Oncol. 22(11):2084-2091.

Leucovorin or a chemical equivalent is administered in a therapeutically effective amount sufficient to increase the effectiveness of 5-FU or a chemical equivalent to treat cancer in a subject and may contain from about 1.0 to 1000 mg/m$^2$/day of compound, for example about 1, 5, 10, 15, 20, 25, 50, 75, 100, 125, 150, 175, 200, 225, 250, 275, 300, 325, 350, 375, 400, 425, 450, 475, 500, 550, 600, 650, 700, 750, 800, 850, 900, 950, to 1000 mg/m$^2$.

Leucovorin or a chemical equivalent may be administered parenterally, e.g., intravenously, intramuscularly, intravenously, subcutaneously, or interperitonically. The carrier or excipient or excipient mixture can be a solvent or a dispersive medium containing, for example, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Except insofar as any conventional media or agent is incompatible with the active ingredient, use in therapeutic compositions is contemplated. Moreover, other or supplementary active ingredients can also be incorporated into the final composition.

Solutions of Leucovorin or a chemical equivalent may be prepared in suitable diluents such as water, ethanol, glycerol, liquid polyethylene glycol(s), various oils, and/or mixtures thereof, and others known to those skilled in the art.

The pharmaceutical forms of Leucovorin or a chemical equivalent suitable for injectable use include sterile solutions, dispersions, emulsions, and sterile powders. The final form must be stable under conditions of manufacture and storage. Furthermore, the final pharmaceutical form must be protected against contamination and must, therefore, be able to inhibit the growth of microorganisms such as bacteria or fungi. A single intravenous or intraperitoneal dose can be administered. Alternatively, a slow long term infusion or multiple short term daily infusions may be utilized, typically lasting from 1 to 8 days. Alternate day or dosing once every several days may also be utilized.

Sterile, injectable solutions are prepared by incorporating a compound in the required amount into one or more appropriate solvents to which other ingredients, listed above or known to those skilled in the art, may be added as required. Sterile injectable solutions are prepared by incorporating the compound in the required amount in the appropriate solvent with various other ingredients as required. Sterilizing procedures, such as filtration, then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

In all cases the final form, as noted, must be sterile and must also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

Prevention or inhibition of growth of microorganisms may be achieved through the addition of one or more antimicrobial agents such as chlorobutanol, ascorbic acid, parabens, thermerosal, or the like. It may also be preferable to include agents that alter the tonicity such as sugars or salts.

In certain embodiments, an effective amount of oxaliplatin or a chemical equivalent is administered to the patient as an enhancing agent or adjuvant. In general, compositions comprising these compounds can be prepared in accordance with known formulation techniques to provide a composition suitable for oral, topical, transdermal, rectal, inhalation, or parenteral (intravenous, intramuscular, or intraperitoneal) administration, and the like. In general the dosing, route of administration, and administration schedule of this compound is well know in the art. Examples of such can be found in, but are not limited to Gramont et al. (2000) J. Clin. Oncol. 18(16):2938-2947 and Cassidy et al. (2004) J. Clin. Oncol. 22(11):2084-2091.

Oxaliplatin or a chemical equivalent is administered in a therapeutically effective amount sufficient to treat cancer in a subject and may contain from about 1.0 to 2000 mg/m$^2$/day of compound, for example about 1, 5, 10, 15, 20, 25, 50, 75, 100, 125, 150, 175, 200, 225, 250, 275, 300, 325, 350, 375, 400, 425, 450, 475, 500, 550, 600, 650, 700, 750, 800, 850, 900, 950, 1000, 1100, 1200, 1300, 1400, 1500, 1600, 1700, 1800, 1900, to 2000 mg/m$^2$.

Oxaliplatin or a chemical equivalent may be administered parenterally, e.g., intravenously, intramuscularly, intravenously, subcutaneously, or interperitonically. The carrier or excipient or excipient mixture can be a solvent or a dispersive medium containing, for example, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Except insofar as any conventional media or agent is incompatible with the active ingredient, use in therapeutic compositions is contemplated. Moreover, other or supplementary active ingredients can also be incorporated into the final composition.

Solutions of oxaliplatin or a chemical equivalent may be prepared in suitable diluents such as water, ethanol, glycerol, liquid polyethylene glycol(s), various oils, and/or mixtures thereof, and others known to those skilled in the art.

The pharmaceutical forms of oxaliplatin or a chemical equivalent suitable for injectable use include sterile solutions, dispersions, emulsions, and sterile powders. The final form must be stable under conditions of manufacture and storage. Furthermore, the final pharmaceutical form must be protected against contamination and must, therefore, be able to inhibit the growth of microorganisms such as bacteria or fungi. A single intravenous or intraperitoneal dose can be administered. Alternatively, a slow long term infusion or multiple short term daily infusions may be utilized, typically lasting from 1 to 8 days. Alternate day or dosing once every several days may also be utilized.

Sterile, injectable solutions are prepared by incorporating a compound in the required amount into one or more appropriate solvents to which other ingredients, listed above or known to those skilled in the art, may be added as required. Sterile injectable solutions are prepared by incorporating the compound in the required amount in the appropriate solvent with various other ingredients as required. Sterilizing procedures, such as filtration, then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

In all cases the final form, as noted, must be sterile and must also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

Prevention or inhibition of growth of microorganisms may be achieved through the addition of one or more antimicrobial agents such as chlorobutanol, ascorbic acid, parabens, thermerosal, or the like. It may also be preferable to include agents that alter the tonicity such as sugars or salts.

In one aspect of the invention, a chemical equivalent of oxaliplatin (a platinum based alkylating agent) selected from the group of, but not limited to Carboplatin and Cisplatin as described in Galanski and Keppler (2007) Anticancer Agents Med. Chem. 7(1):55-73; and BBR3464 as described in Boulikas and Vaugiouka (2003) Oncol. Rep. 10(6):1663-1682, can be used in combination with pyrimidine based antimetabolite and efficacy enhancing agent based chemotherapy to treat patients identified as having the appropriate genetic polymorphism.

In certain embodiments, an effective amount of a pyrimidine based antmetabolite and a platinum-based alkylating agent in adjuvant chemotherapy including, but are not limited to Fluorouracil (5-FU), Leucovorin, and oxaliplatin (FOLFOX) or their chemical equivalents are co-administered to the patient. In general the dosing, route of administration, and administration schedule of these compounds are well know in the art. Examples of such can be found in, but are not limited to Gramont et al. (2000) J. Clin. Oncol. 18(16):2938-2947 and Cassidy et al. (2004) J. Clin. Oncol. 22(11):2084-2091.

In certain embodiments, an effective amount of Irinotecan or a chemical equivalent is administered to the patient as an enhancing agent or adjuvant. Compositions comprising these compounds can be prepared in accordance with known formulation techniques to provide a composition suitable for oral, topical, transdermal, rectal, inhalation, or parenteral (intravenous, intramuscular, or intraperitoneal) administration, and the like. Detailed guidance for preparing compositions of the invention are found by reference to the 18$^{th}$ or 19$^{th}$ Edition of Remington's Pharmaceutical Sciences, Published by the Mack Publishing Co., Easton, Pa. 18040.

Irinotecan or a chemical equivalent is administered in a therapeutically effective amount sufficient to treat cancer in a subject and may contain from about 1.0 to 1000 mg of compound, for example about 1, 5, 10, 15, 20, 25, 50, 75, 100, 125, 150, 175, 200, 225, 250, 275, 300, 325, 350, 375, 400, 425, 450, 475, to 500 mg.

Irinotecan or a chemical equivalent can be administered orally in a suitable formulation as an ingestible tablet, a buccal tablet, capsule, caplet, elixir, suspension, syrup, trouche, wafer, lozenge, and the like. Generally, the most straightforward formulation is a tablet or capsule (individually or collectively designated as an "oral dosage unit"). Suitable formulations are prepared in accordance with a standard formulating techniques available that match the characteristics of the compound to the excipients available for formulating an appropriate composition. A tablet or capsule will contain about 50 to about 500 mg.

Irinotecan or a chemical equivalent may deliver the compound rapidly or may be a sustained-release preparation. The compound may be enclosed in a hard or soft capsule, may be compressed into tablets, or may be incorporated with beverages, food or otherwise into the diet. The percentage of the final composition and the preparations may, of course, be varied and may conveniently range between 1 and 90% of the weight of the final form, e.g., tablet. The amount in such therapeutically useful compositions is such that a suitable dosage will be obtained. An alternative composition according to the current invention are prepared so that an oral dosage unit form contains between about 5 to about 50% by weight (% w) in dosage units weighing between 50 and 1000 mg.

The suitable formulation of an oral dosage unit of Irinotecan or a chemical equivalent may also contain: a binder, such as gum tragacanth, acacia, corn starch, gelatin; sweetening agents such as lactose or sucrose; disintegrating agents such as corn starch, alginic acid and the like; a lubricant such as magnesium stearate; or flavoring such a peppermint, oil of wintergreen or the like. Various other material may be present as coating or to otherwise modify the physical form of the oral dosage unit. The oral dosage unit may be coated with shellac, a sugar or both. Syrup or elixir may contain the compound, sucrose as a sweetening agent, methyl and propylparabens as a preservative, a dye and flavoring. Any material utilized should be pharmaceutically-acceptable and substantially non-toxic. Details of the types of excipients useful may be found in the nineteenth edition of "Remington: The Science and Practice of Pharmacy," Mack Printing Company, Easton, Pa. See particularly chapters 91-93 for a fuller discussion.

Irinotecan or a chemical equivalent may be administered parenterally, e.g., intravenously, intramuscularly, intravenously, subcutaneously, or interperitonically. The carrier or excipient or excipient mixture can be a solvent or a dispersive medium containing, for example, various polar or non-polar solvents, suitable mixtures thereof, or oils. As used herein "carrier" or "excipient" means a pharmaceutically acceptable carrier or excipient and includes any and all solvents, dispersive agents or media, coating(s), antimicrobial agents, iso/hypo/hypertonic agents, absorption-modifying agents, and the like. The use of such substances and the agents for pharmaceutically active substances is well known in the art. Except insofar as any conventional media or agent is incompatible with the active ingredient, use in therapeutic compositions is contemplated. Moreover, other or supplementary active ingredients can also be incorporated into the final composition.

Solutions of Irinotecan or a chemical equivalent may be prepared in suitable diluents such as water, ethanol, glycerol, liquid polyethylene glycol(s), various oils, and/or mixtures thereof, and others known to those skilled in the art.

The pharmaceutical forms of Irinotecan or a chemical equivalent suitable for injectable use include sterile solutions, dispersions, emulsions, and sterile powders. The final form must be stable under conditions of manufacture and storage. Furthermore, the final pharmaceutical form must be protected against contamination and must, therefore, be able to inhibit the growth of microorganisms such as bacteria or fungi. A single intravenous or intraperitoneal dose can be administered. Alternatively, a slow long term infusion or multiple short term daily infusions may be utilized, typically lasting from 1 to 8 days. Alternate day or dosing once every several days may also be utilized.

Sterile, injectable solutions are prepared by incorporating a compound in the required amount into one or more appropriate solvents to which other ingredients, listed above or known to those skilled in the art, may be added as required. Sterile injectable solutions are prepared by incorporating the compound in the required amount in the appropriate solvent with various other ingredients as required. Sterilizing procedures, such as filtration, then follow. Typically, dispersions are made by incorporating the compound into a sterile vehicle which also contains the dispersion medium and the required other ingredients as indicated above. In the case of a sterile powder, the preferred methods include vacuum drying or freeze drying to which any required ingredients are added.

In all cases the final form, as noted, must be sterile and must also be able to pass readily through an injection device such as a hollow needle. The proper viscosity may be achieved and maintained by the proper choice of solvents or excipients. Moreover, the use of molecular or particulate coatings such as lecithin, the proper selection of particle size in dispersions, or the use of materials with surfactant properties may be utilized.

Prevention or inhibition of growth of microorganisms may be achieved through the addition of one or more antimicrobial agents such as chlorobutanol, ascorbic acid, parabens, thermerosal, or the like. It may also be preferable to include agents that alter the tonicity such as sugars or salts.

Usefully, Irinotecan or a chemical equivalent of the invention is solubilized in liposomes. The liposomes may include, for example, lipids such as cholesterol, phospholipids, or micelles comprised of surfactant such as, for example, sodium dodecylsulfate, octylphenolpolyoxyethylene glycol, or sorbitan mono-oleate. Typically, the compound of the invention binds to the lipid bilayer membrane of the liposome with high affinity. The liposome bound prodrug can preferably intercalate between the acyl chains of the lipid. The lactone ring of the camptothecin-derivative, membrane-bound compound of the invention is thereby removed from the aqueous environment inside and outside of the liposome and further protected from hydrolysis. Since the liposome-bound drug is protected from hydrolysis, the antitumor activity of the drug is preserved. If Irinotecan or a chemical equivalent of the invention has a lower affinity for the liposome membrane and thus disassociates from the liposome membrane to reside in the interior of liposome, the pH of the interior of the liposomes may be reduced thereby preventing hydrolysis of such compound of the invention.

U.S. Pat. No. 6,096,336 provides further guidance for preparing liposomal compositions useful in this invention.

In one aspect of the invention, a chemical equivalent of Irinotecan (a topoisomerase I inhibitor) selected from the group of, but not limited to, Campothecine derivatives including CPT-11/Irinotecan, SN-38, APC, NPC, camptothecin, topotecan, exatecan mesylate, 9-nitrocamptothecin, 9-aminocamptothecin, lurtotecan, rubitecan, silatecan, gimatecan, diflomotecan, extatecan, BN-80927, DX-8951f, and MAG-CPT as described in Pommier (2006) Nat. Rev. Cancer 6(10): 789-802 and US Patent Publ. No. 2005/0250854; Protoberberine alkaloids and derivatives thereof including berberrubine and coralyne as described in Li et al. (2000) Biochemistry 39(24):7107-7116 and Gatto et al. (1996) Cancer Res. 15(12):2795-2800; Phenanthroline derivative's including Benzo[i]phenanthridine, Nitidine, and fagaronine as described in Makhey et al. (2003) Bioorg. Med. Chem. 11(8):1809-1820; Terbenzimidazole and derivatives thereof as described in Xu (1998) Biochemistry 37(10):3558-3566; and Anthracycline derivatives including Doxorubicin, Daunorubicin, and Mitoxantrone as described in Foglesong et al. (1992) Cancer Chemother. Pharmacol. 30(2):123-125, Crow et al. (1994) J. Med. Chem. 37(19):3191-3194, and Crespi et al. (1986) Biochem. Biophys. Res. Commun. 136 (2):521-8, can be used in combination therapy with the antibody based chemotherapy described above to treat patients identified as having the appropriate genetic markers.

In another aspect of the invention, dual topoisomerase I and II inhibitors selected from the group of, but not limited to, Saintopin and other Naphthecenediones, DACA and other Acridine-4-Carboxamindes, Intoplicine and other Benzopyridoindoles, TAS-103 and other 7H-indeno[2,1-c]Quinoline-7-ones, Pyrazoloacridine, XR 11576 and other Benzophenazines, XR 5944 and other Dimeric compounds, 7-Oxo-7H-dibenz[f,ij]Isoquinolines and 7-oxo-7H-benzo[e] Perimidines, and Anthracenyl-amino Acid Conjugates as described in Denny and Baguley (2003) Curr. Top. Med. Chem. 3(3):339-353, can be used in combination with pyrimidine based antimetabolite and efficacy enhancing agent based chemotherapy to treat patients identified as having the appropriate genetic polymorphism.

The agents identified herein as effective for their intended purpose can be administered to subjects or individuals identified by the methods herein as suitable for the therapy. Therapeutic amounts can be empirically determined and will vary with the pathology being treated, the subject being treated and the efficacy and toxicity of the agent.

This invention also provides the use of any one or more of the above-described compositions in the preparation of a medicament to treat a patient as identified herein as likely responsive to the administration of this therapy.

Kits

As set forth herein, the invention provides diagnostic methods for determining the type of allelic variant of a polymorphic region present in the gene of interest. In some embodiments, the methods use probes, primers or microarrays comprising nucleotide sequences which are complementary to the polymorphic region of the gene of interest. Accordingly, the invention provides kits for performing these methods as well as instructions for carrying out the methods of this invention such as collecting tissue and/or performing the screen; and/or analyzing the results, and/or administration of an effective amount of the pyrimidine antimetabolite based therapy alone or in combination, such as 5-FU in combination with oxaliplatin or 5-FU in combination with Irinotecan.

In one aspect, the cancer patient is suffering from a cancer of the type of the group: lung cancer, breast cancer, head and neck cancer, ovarian cancer, rectal cancer, colorectal cancer, colon cancer, metastatic colon cancer, advanced colon cancer non-small cell lung cancer (NSCLC), advanced gastric cancer, metastatic gastric cancer, advanced hepatocarcinoma, metastatic and non-metastatic liver cancer, metastatic and non-metastatic intra-abdominal cancer, and non-metastatic bone cancer, metastatic and non-metastatic stomach cancer, metastatic and non-metastatic spleen cancer, metastatic and non-metastatic pancreatic cancer, metastatic and non-metastatic gallbladder cancer or other solid tumors.

In one aspect, the pyrimidine antimetabolite based therapy comprises administration of 5-fluorouracil (5-FU) or an equivalent thereof. In a further aspect, the therapy comprises administration of irinotecan (CPT-11) or an equivalent thereof. In another further aspect, the therapy comprises administration of oxaliplatin or an equivalent thereof.

In one aspect, the therapy is selected from the group consisting of first line therapy, second line therapy, third line therapy, fourth line therapy and fifth line therapy.

In one aspect, the sample comprises a tumor cell, a normal cell adjacent to a tumor, a normal cell corresponding to a tumor tissue type, a blood cell, a peripheral blood lymphocyte or combinations thereof. In another aspect, the sample is at least one of a fixed tissue, a frozen tissue, a biopsy tissue, a resection tissue, a microdissected tissue, a paraffin-embedded tissue or combinations thereof.

In another aspect, the instructions are for determining the genotype by a method comprising PCR, PCR-RFLP, sequencing or microarray.

In one embodiment, the invention provides a kit for determining whether a cancer patient is suitable for a pyrimidine antimetabolite based therapy or alternatively one of the various treatment options described herein. The kits contain one of more of the compositions described above and instructions for use. As an example only, the invention also provides kits for determining response to cancer treatment containing a first and a second oligonucleotide specific for the polymorphic region of the gene. Oligonucleotides "specific for" a genetic locus bind either to the polymorphic region of the locus or bind adjacent to the polymorphic region of the locus. For oligonucleotides that are to be used as primers for amplification, primers are adjacent if they are sufficiently close to be used to produce a polynucleotide comprising the polymorphic region. In one embodiment, oligonucleotides are adjacent if they bind within about 1-2 kb, and preferably less than 1 kb from the polymorphism. Specific oligonucleotides are capable of hybridizing to a sequence, and under suitable conditions will not bind to a sequence differing by a single nucleotide.

Accordingly, the invention provides kits for performing these methods.

The kit can comprise at least one probe or primer which is capable of specifically hybridizing to the polymorphic region of the gene of interest and instructions for use. The kits preferably comprise at least one of the primers described herein. Preferred kits for amplifying at least a portion of the gene of interest comprise two primers, at least one of which is capable of hybridizing to the allelic variant sequence. Such kits are suitable for detection of genotype by, for example, fluorescence detection, by electrochemical detection, or by other detection.

Oligonucleotides, whether used as probes or primers, contained in a kit can be detectably labeled. Labels can be detected either directly, for example for fluorescent labels, or indirectly. Indirect detection can include any detection method known to one of skill in the art, including biotin-avidin interactions, antibody binding and the like. Fluorescently labeled oligonucleotides also can contain a quenching molecule. Oligonucleotides can be bound to a surface. In one embodiment, the preferred surface is silica or glass. In another embodiment, the surface is a metal electrode.

Yet other kits of the invention comprise at least one reagent necessary to perform the assay. For example, the kit can comprise an enzyme. Alternatively the kit can comprise a buffer or any other necessary reagent.

Conditions for incubating a nucleic acid probe or primer with a test sample depend on the format employed in the assay, the detection methods used, and the type and nature of the nucleic acid probe used in the assay. One skilled in the art will recognize that any one of the commonly available hybridization, amplification or immunological assay formats can readily be adapted to employ the nucleic acid probes for use in the present invention. Examples of such assays can be found in Chard (1986) "An Introduction to Radioimmunoassay and Related Techniques" Elsevier Science Publishers, Amsterdam, The Netherlands; Bullock et al., "Techniques in Immunocytochemistry" Academic Press, Orlando, Fla. Vol. 1 (1982), Vol. 2 (1983), Vol. 3 (1985); Tijssen (1985) "Practice and Theory of Immunoassays: Laboratory Techniques in Biochemistry and Molecular Biology", Elsevier Science Publishers, Amsterdam, The Netherlands.

The test samples used in the diagnostic kits include cells, protein or membrane extracts of cells, or biological fluids such as sputum, blood, serum, plasma, or urine. The test sample used in the above-described method will vary based on the assay format, nature of the detection method and the tissues, cells or extracts used as the sample to be assayed. Methods for preparing protein extracts or membrane extracts of cells are known in the art and can be readily adapted in order to obtain a sample which is compatible with the system utilized.

The kits can include all or some of the positive controls, negative controls, reagents, primers, sequencing markers, probes and antibodies described herein for determining the subject's genotype in the polymorphic region of the gene of interest.

As amenable, these suggested kit components may be packaged in a manner customary for use by those of skill in the art. For example, these suggested kit components may be provided in solution or as a liquid dispersion or the like.

Other Uses for the Nucleic Acids of the Invention

The identification of the allele of the gene of interest can also be useful for identifying an individual among other individuals from the same species. For example, DNA sequences can be used as a fingerprint for detection of different individuals within the same species. Thompson and Thompson, eds., (1991) "Genetics in Medicine", W B Saunders Co., Philadelphia, Pa. This is useful, e.g., in forensic studies.

The invention now being generally described, it will be more readily understood by reference to the following examples which are included merely for purposes of illustration of certain aspects and embodiments of the present invention, and are not intended to limit the invention.

EXAMPLE

Evidence is accumulating supporting gender-related differences in the development of colonic carcinomas. Sex steroid hormone receptors are expressed in the colon and interact with epidermal growth factor receptor (EGFR), a gene widely expressed in colonic tissue. Increased EGFR expression is linked with poor prognosis in colon cancer. Within the EGFR gene there are two functional polymorphisms of interest: a polymorphism located at codon 497 (HER-1 R497K) and a dinucleotide $(CA)_n$ repeat polymorphism located within intron 1. These germ-line polymorphisms of EGFR were analyzed in genomic DNA from 318 metastatic colon cancer patients, 177 males and 141 females, collected from 1992 to 2003. Gender-related survival differences were associated with the HER-1 R497K polymorphism ($P_{interaction}=0.003$).

Females with the HER-1 497 Arg/Arg variant had better overall survival (OS) when compared with the Lys/Lys and/or Lys/Arg variants. In males the opposite was true. The EGFR dinucleotide $(CA)_n$ repeat also trended with a gender-related OS difference ($P_{interaction}=0.11$). Females with both short <20 $(CA)_n$ repeat (SEQ ID NO: 3) alleles had better OS than those with any long ≥20 $(CA)_n$ repeats (SEQ ID NO: 4). In males the opposite was true. Combination analysis of the two polymorphisms taken together also revealed the same gender-related survival difference ($P_{interaction}=0.002$). These associations were observed using multivariable analysis. The two polymorphisms were not in linkage disequilibrium and are independent of one another. This study supports the role of functional EGFR polymorphisms as independent prognostic markers in metastatic colon cancer. As a prognostic factor, these variants had opposite prognostic implications based on gender.

Material and Methods

Eligible Patients.

A total of 318 patients with metastatic colon cancer treated at the University of Southern California/Norris Comprehensive Cancer Center (USC/NCCC) or the Los Angeles County/University of Southern California Medical Center (LAC/USCMC), between 1992 and 2003, were eligible for the present study. This population included only metastatic or recurrent colon cancer patients. All patients in this study signed informed consents and enrolled in protocols designed to study the molecular determinants of colon cancer. These protocols permitted blood collection (USC protocol OS-99-10) and/or tissue collection (USC protocol 0S-00-15).

All patients were entered and followed in an institutional database. Patient information was collected through database review and retrospective chart review when additional patient information was necessary. A large number of the patients (69%) were initially treated at an outside institution until, because of failure to respond to prior treatment, they were referred to USC/NCCC or LAC/USCMC for subsequent treatments. The end point of this study, OS, was determined by calculating the difference between the date of first treatment at USC/NCCC or LAC/USC and the date of last follow-up appointment or date of death from disease.

All 318 patients were enrolled in at least one chemotherapy clinical trial while being treated at this institution (USC/NCCC or LAC/USCMC). All patients were treated with 5-fluorouracil (5-FU)-based chemotherapy regimens, and response to chemotherapy was not investigated as an end point for this study. This is a heavily pretreated cohort with 20 (6%) patients treated with one line of chemotherapy, 19 (6%) patients treated with two different chemotherapy regimens, 183 (58%) patients treated with three chemotherapy regimens, and 96 (30%) patients treated with four or more chemotherapy regimens. Although the treatment regimens varied among patients, the majority of the patients were exposed to similar chemotherapies. All 318 patients received treatment with 5-FU, 298 (94%) patients received treatment with 5-FU/irinotecan (CPT-11), and 279 (88%) patients received treatment with 5-FU/oxaliplatin.

DNA Extraction.

Peripheral blood and paraffin-embedded tissue samples were collected from each patient. Genomic DNA was extracted from whole blood cells (WBC) or paraffinized tissue using the QiaAmp kit (Qiagen). Genomic DNA was obtained from peripheral blood for 314 of the patients. There were four samples for which peripheral blood was not available, and therefore genomic DNA was obtained from paraffin-embedded tissue. These 318 genomic DNA samples were used to analyze both polymorphisms.

HER-1 R497K Polymorphism.

The HER-1 R497K polymorphism was analyzed by PCR-RFLP as previously described (18). Briefly, a forward primer 5'-TGCTGTGACCCACTCTGTCT-3' (SEQ ID NO: 5) and a reverse primer 5'-CCAGAAGGTTGCACTTGTCC-3' (SEQ ID NO: 6) were used for PCR amplification. After initial denaturation at 95° C. for 3 min, the reaction was carried out at 94° C. denaturation for 1 min, 59° C. annealing for 1 min, and 72° C. extension for 1 min for 35 cycles. PCR product was digested with BstN1 restriction enzyme (New England Biolabs) at 60° C. overnight and alleles were separated on 4% NuSieve ethidium bromide-stained agarose gel. For quality assurance purposes, 55 (17%) blind duplicate controls were matched. Results for all 55 duplicate controls were identical.

EGFR intron 1 $(CA)_n$ Repeat Polymorphism.

Genotyping of the EGFR CA Microsatellite polymorphisms was analyzed by PCR in combination with fluorescently labeled oligonucleotide primers. Briefly, the region of interest is amplified using a pair of oligonucleotide primers located in the unique flanking region on either side of the microsatellite repeat using primers GC023 for (5'-TGAAGAATTTGAGCCACCCAAA-3' (SEQ ID NO: 7)) and GC023rev (5'-CACTTGAACCAGGGACAGCA-3' (SEQ ID NO: 8)). PCR reaction mix was prepared with HotStart Taq Polymerase (Qiagen) according to the manufacturer's instructions using ~20 ng of genomic DNA, 2 mmol/L $MgCl_2$, and 300 µmol/L of each primer. PCR amplification was done in a thermal cycler (MWG Biotech) using a touchdown protocol with an initial step of 95° C. for 15 min, finishing with 35 cycles of 95° C./25 s, 57° C./1 min, and 72° C./1 min. One of the oligonucleotides (GC023rev) was labeled with 6-FAM and the size of the PCR product, which was directly proportional to the number of repeats, was detected using capillary electrophoresis. A small fraction of the PCR product was mixed with a dye-labeled molecular weight size standard (GS500-ROX, Applied Biosystems, Inc.) and formamide. The samples were denatured by heating to 95° C. for 2 min and then loaded into a model 3730xl DNA Analyzer (Applied Biosystems). Results files were generated for each sample and the size ladder was detected using GeneMapper v3.5 Software (Applied Biosystems). Allele sizes are called automatically, modified manually if required, and output by the GeneMapper software in a tab-delimited format. The size of each allele was then converted into the number of CA repeats using Microsoft Excel. For quality assurance purposes, 92 (29%) blind duplicate controls were matched. Results for all 38 duplicate controls were identical. In addition, 24 negative controls were run and all cases were confirmed negative.

Statistical Analysis.

The primary end point of this study is OS. The OS was determined by calculating the difference between the date of first treatment at USC/NCCC or LAC/USC and the date of last follow-up appointment or date of death. Patients who were alive at the last follow-up were censored at that time.

The associations between sex and other demographic and clinical characteristics were examined using contingency tables and the Fisher exact test. The dominant code for HER-1 R497K was used for the association with OS, and patients who carried heterozygous (Arg/Lys) and homozygous mutant genotypes (Lys/Lys) were grouped together. EGFR intron 1 $(CA)_n$ repeat polymorphism was categorized into two groups: both alleles with <20 $(CA)_n$ (SEQ ID NO: 3) and any alleles with ≥20 $(CA)_n$ (SEQ ID NO: 4) as described previously (19). The associations of HER-1 R497K and EGFR intron 1 $(CA)_n$ repeat polymorphisms with OS were analyzed individually using Kaplan-Meier plots and the log-rank test. The independent effects of two EGFR polymorphisms on OS were examined in multivariable analysis using Cox proportional hazards model. Interactions between sex and EGFR polymorphisms were examined using stratified models and were tested by comparing corresponding likelihood ratio statistics between the baseline and nested Cox proportional hazards models that included the multiplicative product terms (20).

All reported P values were two sided. All analyses were done using the SAS statistical package version 9.0 (SAS Institute, Inc.) and Epilog Plus version 1.0 (Epicenter Software).

RESULTS

This population contained a total of 318 patients, 141 (44%) female and 177 (56%) male. Within the two populations, males and females, there were no statistically significant variations with regard to age, racial/ethnic make-up, location of the primary tumor, or location of first metastatic site. The median age at the time of diagnosis was 58 years (range, 25-86 years). The racial/ethnic distribution of study participants was 234 (73%) Caucasian, 43 (14%) Asian, 24 (8%) Hispanic, 15 (5%) Black, and 2 (1%) Native American. The location of the primary tumor within the colon was as follows: 144 (54%) left-sided tumors, 124 (46%) right-sided tumors, and 51 with the side unknown. The location of the first metastatic site was 156 (49%) liver, 56 (18%) intra-abdominal, and 46 (15%) other (lung, bone, stomach, spleen, pancreas, or gallbladder); there were 57 (18%) patients that presented with two or more metastatic sites at the onset of metastatic disease (Table 2).

TABLE 2

Demographic and baseline clinical information by sex

| | Total, n (%) | Female, n (%) | Male, n (%) | P* |
|---|---|---|---|---|
| n | 318 | 141 | 177 | 0.24 |
| Age, median (range), y | 58 (25-86) | 57 (25-82) | 59 (25-86) | |
| ≤39 | 28 (9) | 16 (11) | 12 (7) | |
| 40-59 | 144 (45) | 66 (47) | 78 (44) | |
| 60+ | 146 (46) | 59 (42) | 87 (49) | |
| Ethnic | | | | |
| Asian | 43 (14) | 24 (17) | 19 (11) | 0.27 |
| Black | 15 (5) | 6 (4) | 9 (5) | |
| Hispanic | 24 (8) | 7 (5) | 17 (10) | |
| Native American | 2 (1) | 1 (1) | 1 (1) | |
| Side of tumor | | | | |
| Left | 144 (54) | 62 (50) | 82 (57) | 0.27 |
| Right | 124 (46) | 62 (50) | 62 (43) | |
| Unknown | 50 | 17 | 33 | |
| No. first metastatic sites 1 | | | | |
| Liver | 156 (49) | 65 (46) | 91 (52) | 0.60 |
| Intra-abdominal | 56 (18) | 28 (20) | 28 (16) | |
| Other | 46 (15) | 19 (14) | 27 (15) | |
| 2+ | 57 (18) | 28 (20) | 29 (17) | |
| Unknown | 3 | 1 | 2 | |

*Based on Fisher's exact test.

OS differences in this population were not associated with gender differences, racial/ethnic distribution, location of primary tumor, or location of first metastatic lesion (data not shown). The EGFR polymorphisms were not associated with the age of onset of metastatic disease, location of primary tumor, or location of first metastatic lesion (data not shown).

HER-1 R497K Polymorphism.

The extracted genomic DNA was evaluated for HER-1 R497K polymorphism and the assay was successful in 316 of the 318 cases. There were two cases where the genomic DNA was either consumed or degraded. Fifty percent (157 of 316) of the patients had the Arg/Arg variant and 50% (159 of 316) of the patients had the Arg/Lys or the Lys/Lys variant. The allelic distribution of this polymorphism did not vary among the gender groups (Table 3). This distribution is consistent with other published findings (19). Asians were more likely to carry the Lys allele compared with other racial/ethnic groups (Table 3).

cessful in 311 of the 318 cases. There were seven cases where the genomic DNA was either consumed or degraded. Three hundred eleven successful cases were analyzed for the $(CA)_n$ repeat polymorphism in relation to patient OS.

Alleles with each of the previously reported $(CA)_n$ repeat lengths were observed (n=14-23) (SEQ ID NO: 9). In addition, novel $(CA)_n$ repeat lengths of n=24 (SEQ ID NO: 10) and 28 (SEQ ID NO: 11) were also found. Heterozygosity in this series was 72.7% (226 of 311). There were 39 different repeat EGFR genotypes that could be determined with frequencies ranging between 0.003 and 0.19. The most common genotypes in this study were 16/20, 16/18, 16/16, and 20/20. The most frequent alleles in this cohort were $(CA)_{16}$ (SEQ ID NO: 1), $(CA)_{20}$ (SEQ ID NO: 12), and $(CA)_{18}$ (SEQ ID NO:

TABLE 3

Association of polymorphisms and overall survival (Table 3 discloses "$(CA)_n$ repeats <20" as SEQ ID NO: 3 and "$(CA)_n$ repeats ≥20" as SEQ ID NO: 4.)

| | Female | | | Male | | | |
|---|---|---|---|---|---|---|---|
| EGFR polymorphism | N | Median survival (95% CI), mo | RR (95% CI) | N | Median survival (95% CI), mo | RR (95% CI) | $P_{interaction}$ |
| HER-1 R497K | | | | | | | |
| Arg/Arg | 67 | 16.0 (13.5-19.2) | 1 (reference) | 90 | 10.3 (9.0-13.5) | 1 (reference) | |
| Lys allele | 74 | 14.0 (11.2-17.9) | 1.41 (0.94-2.10) | 85 | 13.7 (10.8-19.1) | 0.64 (0.46-0.89) | |
| Adjusted P | | 0.093* | | | 0.007* | | 0.003‡ |
| EGFR $(CA)_n$ repeat | | | | | | | |
| Both $(CA)_n$ repeats <20 | 65 | 17.6 (13.7-22.7) | 1 (reference) | 78 | 10.3 (8.3-15.5) | 1 (reference) | |
| Any $(CA)_n$ repeats ≥20 | 72 | 14.1 (12.1-18.3) | 1.37 (0.93-2.01) | 96 | 13.1 (10.7-16.0) | 0.92 (0.67-1.28) | |
| Adjusted P | | 0.11* | | | 0.63* | | 0.11‡ |
| Combined analysis | | | | | | | |
| Arg/Arg and $(CA)_n$ <20 | 31 | 15.7 (11.5-41.4) | 1 (reference) | 43 | 8.9 (7.3-11.4) | 1 (reference) | |
| Arg/Arg and $(CA)_n$ ≥20 or Lys and $(CA)_n$ <20 | 69 | 17.3 (14.0-19.2) | 0.93 (0.56-1.54) | 81 | 13.1 (10.3-17.5) | 0.84 (0.57-1.25) | |
| Lys and $(CA)_n$ ≥20 | 37 | 12.2 (7.7-16.7) | 1.90 (1.10-3.29) | 50 | 13.6 (10.7-19.5) | 0.62 (0.39-0.97) | |
| Adjusted P | | 0.008* | | | 0.094* | | 0.002‡ |

Abbreviations:
RR. relative risk:
95% CI. 95% confidence interval.
*Based on Cox proportional hazards model: adjusted by age and previous treatments.
‡Based on the likelihood ratio test; adjusted by age and previous treatments.

The HER-1 R497K genotypes were analyzed with regard to OS. When the population was not separated by gender, the genotypes were not associated with OS (data not shown). However, when the patient population was separated by gender, the polymorphic variants of HER-1 R497K were associated with OS ($P_{interaction}$=0.003, likelihood ratio test). Male patients with the Arg/Arg variant (n=90) had shorter OS (median OS, 10.3 months) than male patients with the Arg/Lys or the Lys/Lys variant (n=85; median OS, 13.7 months; Table 3). In female patients the opposite OS difference was found. Female patients with the Arg/Arg variant (n=67) had longer OS (median OS, 16.0 months) than female patients with the Arg/Lys or the Lys/Lys variant (n=74; median OS, 14.0 months; Table 3). Therefore, as a prognostic factor, these HER-1 R497K polymorphic variants had opposite implications based on gender.

Patients with the Arg/Arg variant had a large shift in OS based on whether the patients were male (OS of 10.3 months; n=90) or female (OS of 16.0 months; n=67; Table 3; FIG. 1). However, in patients with the Arg/Lys or the Lys/Lys variant, median OS remained nearly constant: males, 13.7 months (n=85); females, 14.0 months (n=74; Table 3).

EGFR Intron 1 $(CA)_n$ Repeat Polymorphism.

The extracted genomic DNA was evaluated for the EGFR intron 1 $(CA)_n$ repeat polymorphism and the assay was suc- 13). Asians were more likely to carry the longer $(CA)_n$ repeats compared with Whites, Blacks, and Hispanics (Table 3). These frequency distributions are consistent with those of previous studies (19, 21).

To evaluate the effect the number of $(CA)_n$ repeats had on OS among all study participants, the total of 311 patients were divided into two subgroups: 143 (46%) patients that possessed both $(CA)_n$ repeats <20 (short) (SEQ ID NO: 3) and 168 (54%) patients that had any $(CA)_n$ repeats ≥20 (long) (SEQ ID NO: 4). Without separation of the patients according to gender, there were no statistically significant associations (data not shown). However, when the patient population was separated by gender, the $(CA)_n$ repeat genotypes were associated with OS ($P_{interaction}$=0.11, likelihood ratio test; Table 3).

The male patients with two short <20 $(CA)_n$ (SEQ ID NO: 3) repeat alleles (n=78) had a shorter OS (median OS, 10.3 months) compared with males that had any long ≥20 $(CA)_n$ (SEQ ID NO: 4) repeat allele (n=96; median OS, 13.1 months; Table 3). In female patients the opposite OS difference was found. Female patients with two short <20 $(CA)_n$ (SEQ ID NO: 3) repeat alleles (n=65) had longer OS (median OS, 17.6 months) compared with the female patient group that had any long ≥20 $(CA)_n$ repeat allele (SEQ ID NO: 4)

(n=72; median OS, 14.1 months; Table 3). Therefore, as a prognostic factor, this EGFR intron 1 $(CA)_n$ repeat polymorphism had opposite implications based on gender.

Figure 2:
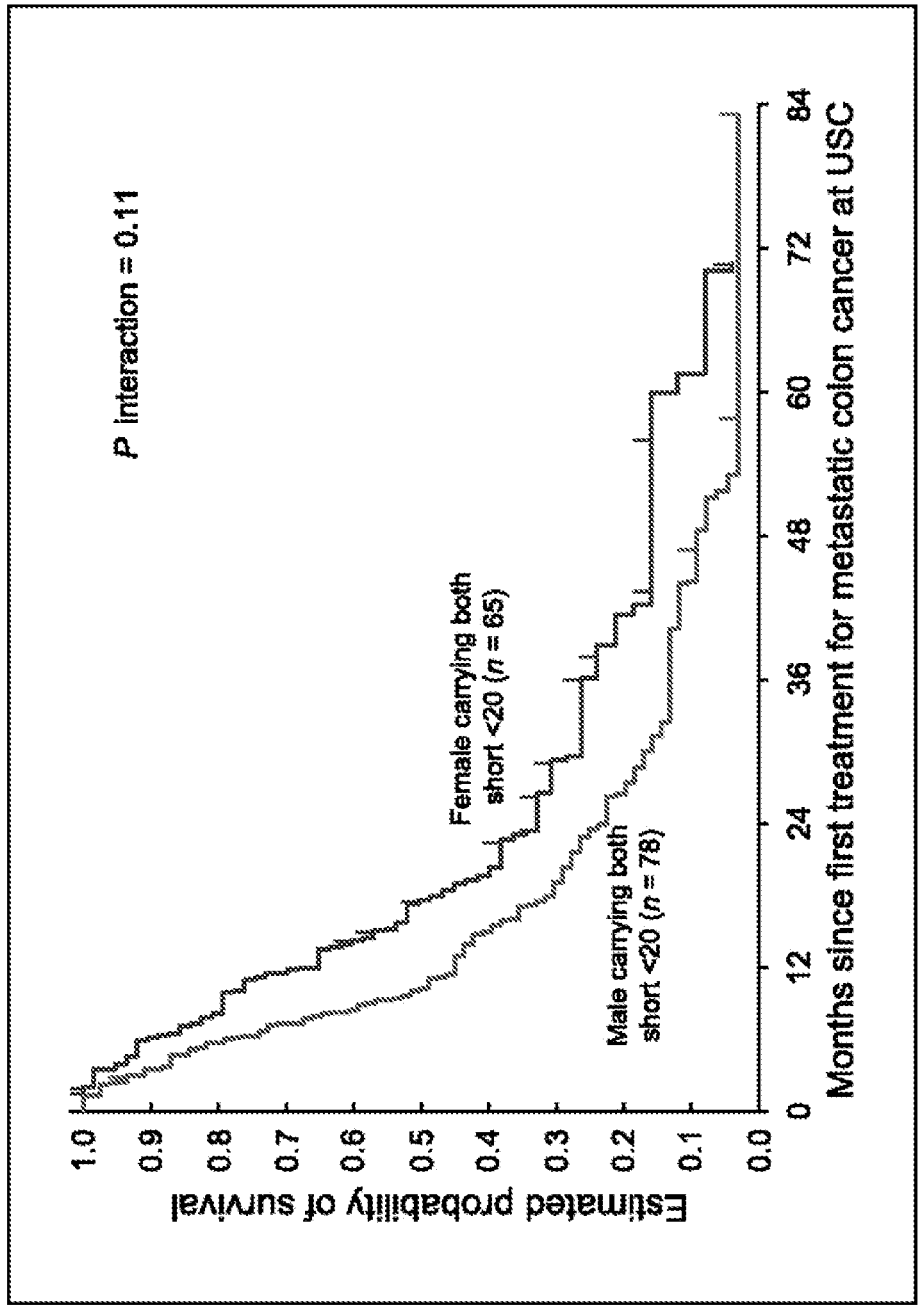
FIG. 2 shows gender-related overall survival associated with the EGFR intron 1 $(CA)_n$ repeat with both short alleles of <20 $(CA)_n$ repeats (SEQ ID NO: 3) genotype. The top curve indicates female patients carrying both short alleles of <20 $(CA)_n$ repeats (SEQ ID NO: 3), while the bottom curve indicates male patients carrying both short alleles of <20 $(CA)_n$ repeats (SEQ ID NO: 3). The designation n represents the number of patients. The X-axis indicates the number of months since a patient first received treatment for metastatic colon cancer at the University of Southern California (USC). The Y-axis indicates the estimated probability of survival. The P interaction value is equal to 0.11.

Patients with both short <20 $(CA)_n$ repeat alleles (SEQ ID NO: 3) showed a large shift in OS based on whether the patient was male (median OS, 10.3 months; n=78) or female (median OS, 17.9 months; n=65; Table 3; FIG. 2). However, patients with any long ≥20 $(CA)_n$ repeat allele (SEQ ID NO: 4) had their median OS remaining nearly constant: males, 13.1 months (n=96); females, 14.1 months (n=72; Table 3).

Combination Analysis.

Figure 3:
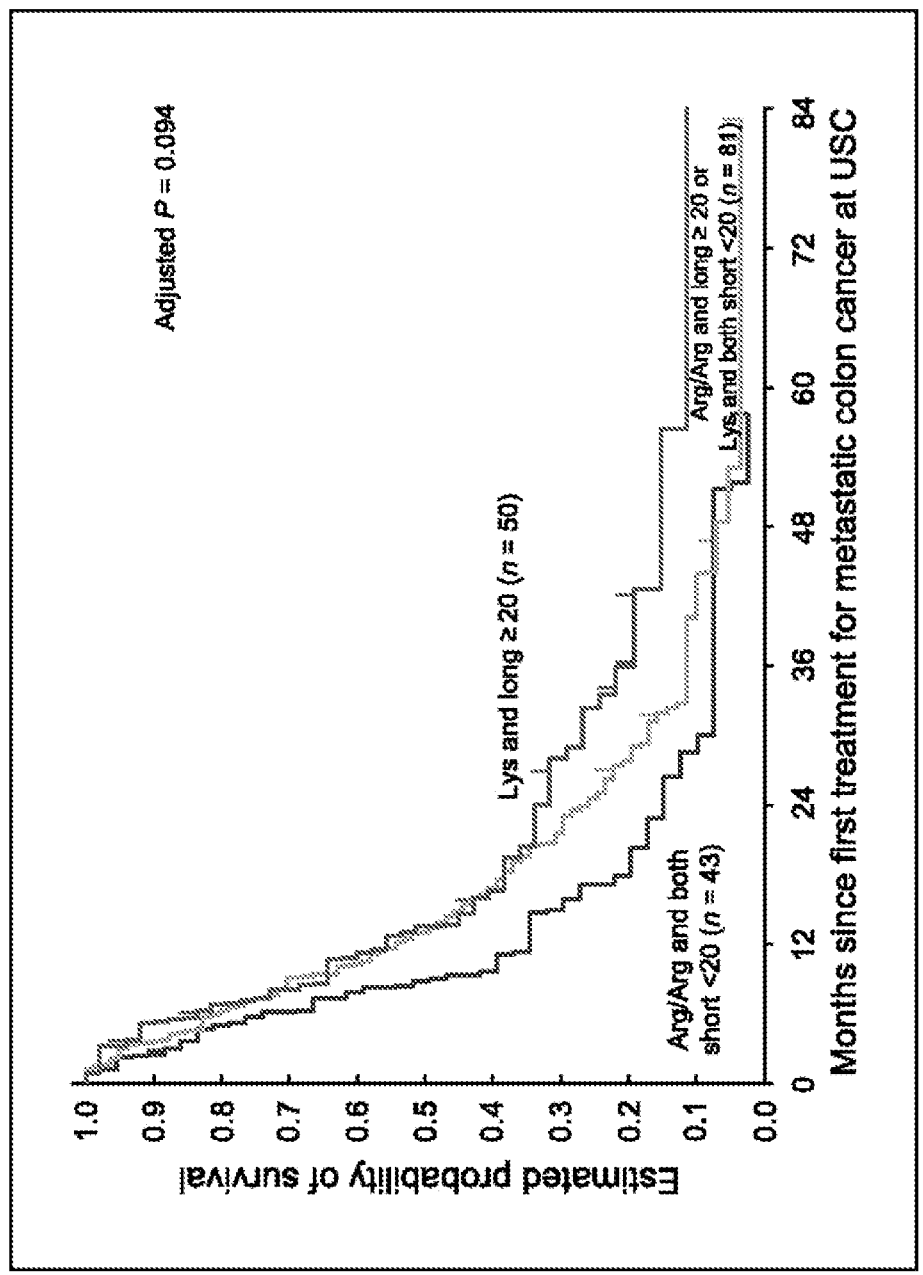
FIG. 3 shows the combined analysis of overall survival for male patients having both HER-1 (R497K) and EGFR intron 1 (CA)$_n$ repeat polymorphisms. The top curve indicates male patients carrying at least one Lys allele for HER-1 and at least one long ≥20 allele for EGFR intron 1 (CA)$_n$ repeat. The middle curve indicates male patients carrying Arg/Arg for HER-1 and at least one long ≥20 allele for EGFR intron 1 (CA)$_n$ repeat or carrying at least one Lys allele for HER-1 and both short alleles of <20 (CA)$_n$ repeats (SEQ ID NO: 3) for EGFR intron 1 (CA)$_n$ repeat. The bottom curve indicates male patients carrying Arg/Arg for HER-1 and both short alleles of <20 (CA)$_n$ repeats (SEQ ID NO: 3) for EGFR intron 1 (CA)$_n$ repeat. The designation n represents the number of patients. The X-axis indicates the number of months since a patient first received treatment for metastatic colon cancer at the University of Southern California (USC). The Y-axis indicates the estimated probability of survival. The adjusted P value is equal to 0.094.
Figure 4:
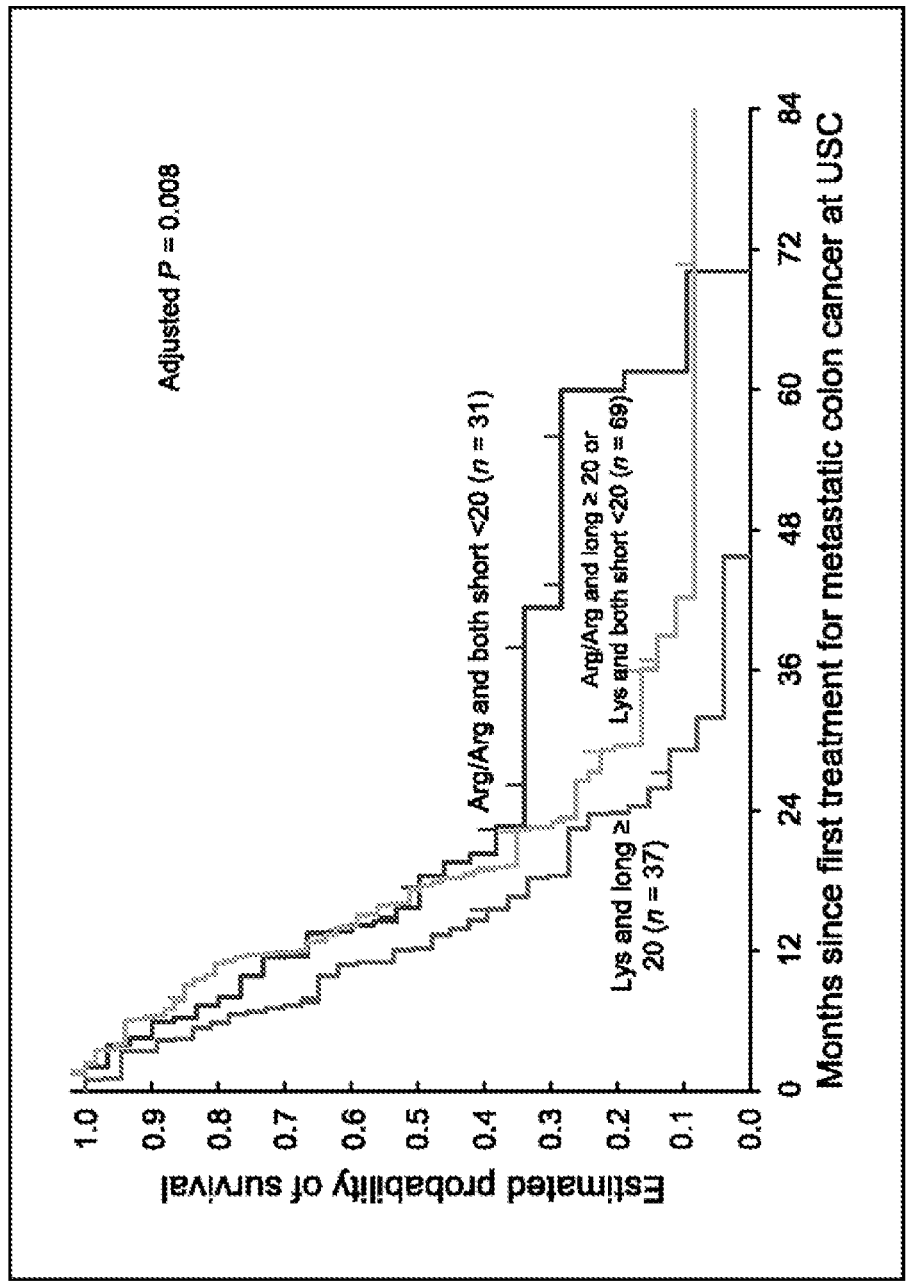
FIG. 4 shows the combined analysis of overall survival for female patients having both HER-1 (R497K) and EGFR intron 1 (CA)$_n$ repeat polymorphisms. The top curve indicates female patients carrying Arg/Arg for HER-1 and both short alleles of <20 (CA)$_n$ repeats (SEQ ID NO: 3) for EGFR intron 1 (CA)$_n$ repeat. The middle curve indicates female patients carrying Arg/Arg for HER-1 and at least one long ≥20 allele for EGFR intron 1 (CA)$_n$ repeat or carrying at least one Lys allele for HER-1 and both short alleles of <20 (CA)$_n$ repeats (SEQ ID NO: 3) for EGFR intron 1 (CA)$_n$ repeat. The bottom curve indicates female patients carrying at least one Lys allele for HER-1 and at least one long ≥20 allele for EGFR intron 1 (CA)$_n$ repeat. The designation n represents the number of patients. The X-axis indicates the number of months since a patient first received treatment for metastatic colon cancer at the University of Southern California (USC). The Y-axis indicates the estimated probability of survival. The adjusted P value is equal to 0.008.

The two EGFR polymorphisms were analyzed together using combination analysis. Again, the polymorphic variants were associated with opposite implications for survival based on gender ($P_{interaction}$=0.002, likelihood ration test; Table 3). Males with any long ≥20 $(CA)_n$ repeat allele (SEQ ID NO: 4) and the HER-1 Lys/Lys or Arg/Lys variant had statistically significant better survival (OS of 13.6 months) than the males with two short <20 $(CA)_n$ repeat alleles (SEQ ID NO: 3) and the HER-1 Arg/Arg variant (OS of 8.9 months; adjusted P=0.094; FIG. 3). In the female population the opposite was found. Females with any long ≥20 $(CA)_n$ repeat allele (SEQ ID NO: 4) and the HER-1 Lys/Lys or Arg/Lys variant had statistically significant shorter OS (12.2 months) than the females with two short <20 $(CA)_n$ repeat alleles (SEQ ID NO: 3) and the HER-1 Arg/Arg variant (15.7 months; adjusted P=0.008; FIG. 4). As a prognostic factor in combination these two EGFR polymorphic variants had opposite implications based on gender.

Linkage Disequilibrium.

The HER-1 R497K and the EGFR$(CA)_n$ repeat polymorphisms showed no statistically significant evidence of linkage disequilibrium in this patient population (data not shown).

DISCUSSION

The HER-1 R497K polymorphic variant was associated with longer survival in females but with shorter survival in males. A previous in vitro study has shown that this HER-1 R497K polymorphism is related to attenuated ligand binding, reduced growth stimulation, diminished tyrosine kinase activation, and limited induction of proto-oncogenes. The "wild-type" Arg/Arg genotype does not cause this loss of EGFR ligand binding (6). Activation of EGFR in colon cancer is associated with a worse prognosis (4). Therefore, the Arg/Arg genotype would be expected to be associated with a worse prognosis. The males in this study did show this association [i.e., the Arg/Arg genotype (OS, 10.3 months) had a worse prognosis]. In contrast, the opposite was observed for females with the Arg/Arg genotype who had a better prognosis (OS, 16.0 months). This gender-related survival difference in the HER-1 R497K polymorphism in colon cancer is novel. The exact mechanistic interactions that contribute to this observed association are currently unclear.

The other EGFR polymorphism, the dinucleotide $(CA)_n$ repeat, also had opposite OS associations based on gender. This variant was associated with longer survival in females and with shorter survival in males. Previous in vitro and in vitro studies have shown this EGFR dinucleotide $(CA)_n$ repeat polymorphism to effect the expression of EGFR. These studies have shown that shorter $(CA)_n$ repeat lengths, <20 base-pairs long (SEQ ID NO: 14), have higher expression of EGFR (7, 8). High expression of EGFR in the colon is a known poor prognostic factor (4). Therefore, the patients with the shorter $(CA)_n$ repeat variants are expected to have a worse prognosis. The males in the study population did show a clinical outcome that was consistent with these previous findings; males with two short <20 repeat alleles had a worse prognosis (OS, 10.4 months). However, the opposite was observed in females. Females with the two short <20 repeat alleles had a better prognosis (OS, 17.6 months). This gender-related survival difference for this $(CA)_n$ dinucleotide polymorphism in colon cancer is novel. The exact mechanistic interactions that contribute to this observed association are unclear.

The HER-1 R497K and the EGFR dinucleotide $(CA)_n$ repeat polymorphisms had no evidence of linkage disequilibrium in this patient population. Despite their genetic independence, the two EGFR polymorphisms displayed similar gender-related inverse OS associations using combination statistical analysis. Again, the polymorphic variants were associated with longer survival in the females but were associated with shorter survival in the males. Therefore, they have opposite prognostic value based on gender and are independent of one another.

In this study, the male population had findings consistent with the literature (4, 6-8). However, the female population in this study had exactly the opposite findings from those in the male population and from the prior literature (4, 6-8). In the female population, both variant EGFR polymorphisms, previously described as poor prognostic markers and previously associated with high expression and/or ligand binding of EGFR (6-8), showed an unexpected survival benefit.

This study has shown for the first time that functional polymorphisms of EGFR are inversely related to gender-specific OS in patients with metastatic colon cancer. Gender differences in this population are important. When the study population was not separated by gender, the EGFR polymorphisms were not associated with survival; when the population was separated by gender, associations with survival were observed. This shows the potential importance of analyzing colon cancer data both with and without gender as a stratifying factor.

EGFR activation of its signaling pathways may occur through intermediaries that result in different activation in males and females. Because the colon expresses both estrogen receptor β (14) and androgen receptor (15), and EGFR interacts with both steroid hormone receptor pathways (16, 17), EGFR may have molecular intermediates that interact in a gender-specific way to effect EGFR pathway activation.

The design of this study is such that information about menopausal status, use of estrogen replacement therapy, and the relative amount of sex hormones present in each patient at the time of treatment was not known. Therefore, it is not possible to address the potential importance of sex steroid hormones in this patient population. Additional studies are warranted to determine the molecular reasons for the observations made in this study.

This study may have implications for treatment of males and females with metastatic colon cancer. A phase III clinical trial (European Organization for Research and Treatment of Cancer 05963) comparing two different chemotherapy regimens for optimal dynamic scheduling of oxaliplatin, 5-FU, and leucovorin in metastatic colorectal cancer patients showed no survival differences until the population was separated by gender (22). In this study, gender was associated with a treatment-specific inversion of OS benefit among males and females. Another study indicated that females with colorectal cancer are more likely to respond to 5-FU-based chemotherapy compared with males (23). Therefore, gender-related, treatment-specific differences in the colon have been shown. These differences may be due to different chemosensitivities resulting from hormonal variations among genders.

This study has shown that EGFR polymorphic variations are associated with gender-related OS differences.

In summary, this study supports the role of functional polymorphisms of EGFR as independent prognostic markers in metastatic colon cancer with opposite prognostic implications in males and females. To Applicant's knowledge, this is the first study that shows a relationship between EGFR gene polymorphisms and gender-related survival.

It is to be understood that while the invention has been described in conjunction with the above embodiments, and has been previously described in Press (2008) Cancer Res. 68(8):3037-3042, incorporated by reference in its entirety, that the foregoing description and examples are intended to illustrate and not limit the scope of the invention. Other aspects, advantages and modifications within the scope of the invention will be apparent to those skilled in the art to which the invention pertains.

LIST OF REFERENCES

1. Jemal A, Siegel R, Ward E, Murray T, Xu J, Thun M J. Cancer statistics, 2007. CA Cancer J Clin 2007; 57:43-66.
2. Goldstein N S, Armin M. Epidermal growth factor receptor immunohistochemical reactivity in patients with American Joint Committee on Cancer Stage 1V colon adenocarcinoma: implications for a standardized scoring system. Cancer 2001; 92:1331-46.
3. Laskin J J, Sandler A B. Epidermal growth factor receptor: a promising target in solid tumours. Cancer Treat Rev 2004; 30:1-17.
4. Hemming A W, Davis N L, Kluftinger A, et al. Prognostic markers of colorectal cancer: an evaluation of DNA content, epidermal growth factor receptor, and Ki-67. J Surg Oncol 1992; 51:147-52.
5. Saltz L B, Meropol N J, Loehrer P J, Sr., Needle M N, Kopit J, Mayer R J. Phase II trial of cetuximab in patients with refractory colorectal cancer that expresses the epidermal growth factor receptor. J Clin Oncol 2004; 22:1201-8.
6. Moriai T, Kobrin M S, Hope C, Speck L, Korc M. A variant epidermal growth factor receptor exhibits altered type a transforming growth factor binding and transmembrane signaling. Proc Natl Acad Sci USA 1994; 91:10217-21.
7. Buerger H, Gebhardt F, Schmidt H, et al. Length and loss of heterozygosity of an intron 1 polymorphic sequence of egfr is related to cytogenetic alterations and epithelial growth factor receptor expression. Cancer Res 2000; 60:854-7.
8. Gebhardt F, Zanker K S, Brandt B. Modulation of epidermal growth factor receptor gene transcription by a polymorphic dinucleotide repeat in intron 1. J Biol Chem 1999; 274:13176-80.
9. Ries L A, Wingo P A, Miller D S, et al. The annual report to the nation on the status of cancer, 1973-1997, with a special section on colorectal cancer. Cancer 2000; 88:2398-424.
10. Wingo P A, Ries L A, Rosenberg H M, Miller D S, Edwards B K. Cancer incidence and mortality, 1973-1995: a report card for the U.S. Cancer 1998; 82:1197-207.
11. DeCosse J J, Ngoi S S, Jacobson J S, Cennerazzo W J. Gender and colorectal cancer. Eur J Cancer Prev 1993; 2:105-15.
12. Rossouw J E, Anderson G L, Prentice R L, et al. Risks and benefits of estrogen plus progestin in healthy postmenopausal women: principal results From the Women's Health Initiative randomized controlled trial. JAMA 2002; 288: 321-33.
13. Grodstein F, Newcomb P A, Stampfer M J. Postmenopausal hormone therapy and the risk of colorectal cancer: a review and meta-analysis. Am J Med 1999; 106:574-82.
14. Fiorelli G, Picariello L, Martineti V, Tonelli F, Brandi M L. Functional estrogen receptor β in colon cancer cells. Biochem Biophys Res Commun 1999; 261:521-7.
15. Catalano M G, Pfeffer U, Raineri M, et al. Altered expression of androgen-receptor isoforms in human colon-cancer tissues. Int J Cancer 2000; 86:325-30.
16. Levin E R. Bidirectional signaling between the estrogen receptor and the epidermal growth factor receptor. Mol Endocrinol 2003; 17:309-17.
17. Bonaccorsi L, Muratori M, Carloni V, et al. The androgen receptor associates with the epidermal growth factor receptor in androgen-sensitive prostate cancer cells. Steroids 2004; 69:549-52.
18. Martin K, Radlmayr M, Borchers R, Heinzlmann M, Folwaczny C. Candidate genes colocalized to linkage regions in inflammatory bowel disease. Digestion 2002; 66:121-6.
19. Zhang W, Park D J, Lu B, et al. Epidermal growth factor receptor gene polymorphisms predict pelvic recurrence in patients with rectal cancer treated with chemoradiation. Clin Cancer Res 2005; 11:600-5.
20. Rothman K J G S. Modern epidemiology. Philiadelphia: Lippincott-Raven; 1998.
21. Liu W, Innocenti F, Chen P, Das S, Cook E H, Jr., Ratain M J. Interethnic difference in the allelic distribution of human epidermal growth factor receptor intron 1 polymorphism. Clin Cancer Res 2003; 9:1009-12.
22. Lévi F, Gorlia T, Tubiana N, et al. Gender as a predictor for optimal dynamic scheduling of oxaliplatin, 5-fluorouracil and leucovorin in patients with metastatic colorectal cancer. Results from EORTC randomized phase HI trial 05963. J Clin Oncol (Meeting Abstracts) 2005; 23:[abstract #3587].
23. Elsaleh H, Joseph D, Grieu F, Zeps N, Spry N, Iacopetta B. Association of tumour site and sex with survival benefit from adjuvant chemotherapy in colorectal cancer. Lancet 2000; 355:1745-50.

What is claimed is:

1. A method for identifying and treating a female colon cancer patient suitable for a pyrimidine antimetabolite based therapy, comprising screening a cell or tissue sample isolated from the patient for the EGFR polymorphism of R497K and administering an effective amount of the therapy to a patient having the genotype of Arg/Arg for R497K.

2. The method of claim 1, wherein the colon cancer patient suffers from metastatic colon cancer or advanced colon cancer.

3. The method of claim 1, wherein the colon patient identified as suitable for the therapy and treated is a patient more likely to experience longer overall survival as compared to a patient not suitable for the therapy.

4. The method of claim 1, wherein the patient was identified by a method comprising screening a cell or tissue sample isolated from the patient for the EGFR polymorphism of R497K.

5. The method of claim 1 or 2, wherein the pyrimidine antimetabolite based therapy comprises administration of 5-fluorouracil (5-FU) or a chemical equivalent thereof.

6. The method of claim 5, wherein the therapy further comprises administration of irinotecan (CPT-11) or a chemical equivalent thereof.

7. The method of claim 5, wherein the therapy further comprises administration of oxaliplatin or a chemical equivalent thereof.

8. The method of claim 1 or 2, wherein the therapy is selected from the group consisting of first line therapy, second line therapy, third line therapy, fourth line therapy and fifth line therapy.

9. The method of claim 1 or 2, wherein the sample comprises a tumor cell, a normal cell adjacent to a tumor, a normal cell corresponding to a tumor tissue type, a blood cell, a peripheral blood lymphocyte or combinations thereof.

10. The method of claim 1 or 2, wherein the sample is at least one of a fixed tissue, a frozen tissue, a biopsy tissue, a resection tissue, a microdissected tissue, a paraffin-embedded tissue or combinations thereof.

11. The method of claim 1 or 2, wherein the genotype is determined by a method comprising PCR, PCR-RFLP, sequencing or microarray.

12. The method of claim 1 or 2, wherein the patient is a human patient.

* * * * *

SEQUENCE LISTING

<160> NUMBER OF SEQ ID NOS: 14

<210> SEQ ID NO 1
<211> LENGTH: 32
<212> TYPE: DNA
<213> ORGANISM: Homo sapiens

<400> SEQUENCE: 1
cacacacaca cacacacaca cacacacaca ca                32

-continued

```
<210> SEQ ID NO 2
<211> LENGTH: 42
<212> TYPE: DNA
<213> ORGANISM: Homo sapiens
<220> FEATURE:
<223> OTHER INFORMATION: See specification as filed for detailed
      description of substitutions and preferred embodiments

<400> SEQUENCE: 2
cacacacaca cacacacaca cacacacaca cacacacaca ca                          42

<210> SEQ ID NO 3
<211> LENGTH: 38
<212> TYPE: DNA
<213> ORGANISM: Homo sapiens
<220> FEATURE:
<221> NAME/KEY: misc_feature
<222> LOCATION: (1)..(38)
<223> OTHER INFORMATION: This sequence may encompass 0-19 "ca" repeating
      units

<400> SEQUENCE: 3
cacacacaca cacacacaca cacacacaca cacacaca                               38

<210> SEQ ID NO 4
<211> LENGTH: 40
<212> TYPE: DNA
<213> ORGANISM: Homo sapiens
<220> FEATURE:
<223> OTHER INFORMATION: See specification as filed for detailed
      description of substitutions and preferred embodiments

<400> SEQUENCE: 4
cacacacaca cacacacaca cacacacaca cacacacaca                             40

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgctgtgacc cactctgtct                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccagaaggtt gcacttgtcc                                                   20

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tgaagaattt gagccaccca aa                                                22
```

-continued

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cacttgaacc agggacagca                                              20

<210> SEQ ID NO 9
<211> LENGTH: 46
<212> TYPE: DNA
<213> ORGANISM: Homo sapiens
<220> FEATURE:
<221> NAME/KEY: misc_feature
<222> LOCATION: (1)..(46)
<223> OTHER INFORMATION: This sequence may encompass 14-23 "ca"
      repeating units

<400> SEQUENCE: 9
cacacacaca cacacacaca cacacacaca cacacacaca cacaca                 46

<210> SEQ ID NO 10
<211> LENGTH: 48
<212> TYPE: DNA
<213> ORGANISM: Homo sapiens

<400> SEQUENCE: 10
cacacacaca cacacacaca cacacacaca cacacacaca cacacaca               48

<210> SEQ ID NO 11
<211> LENGTH: 56
<212> TYPE: DNA
<213> ORGANISM: Homo sapiens

<400> SEQUENCE: 11
cacacacaca cacacacaca cacacacaca cacacacaca cacacacaca cacaca      56

<210> SEQ ID NO 12
<211> LENGTH: 40
<212> TYPE: DNA
<213> ORGANISM: Homo sapiens

<400> SEQUENCE: 12
cacacacaca cacacacaca cacacacaca cacacacaca                        40

<210> SEQ ID NO 13
<211> LENGTH: 36
<212> TYPE: DNA
<213> ORGANISM: Homo sapiens

<400> SEQUENCE: 13
cacacacaca cacacacaca cacacacaca cacaca                            36

<210> SEQ ID NO 14
<211> LENGTH: 18
<212> TYPE: DNA
<213> ORGANISM: Homo sapiens
<220> FEATURE:
<221> NAME/KEY: misc_feature

```
<222> LOCATION: (1)..(18)
<223> OTHER INFORMATION: This sequence may encompass 0-9 "ca" repeating
      units

<400> SEQUENCE: 14
cacacacaca cacacaca                                                    18
```